United States Patent
Tyson, II

(10) Patent No.: US 11,529,774 B2
(45) Date of Patent: Dec. 20, 2022

(54) IN-SITU MONITORING OF THERMOFORMABLE COMPOSITES

(71) Applicant: John Tyson, II, King of Prussia, PA (US)

(72) Inventor: John Tyson, II, King of Prussia, PA (US)

(*) Notice: Subject to any disclaimer, the term of this patent is extended or adjusted under 35 U.S.C. 154(b) by 140 days.

(21) Appl. No.: 16/779,596

(22) Filed: Feb. 1, 2020

(65) Prior Publication Data

US 2020/0230899 A1 Jul. 23, 2020

Related U.S. Application Data

(63) Continuation-in-part of application No. 16/236,081, filed on Dec. 28, 2018, and a continuation-in-part of application No. 16/236,072, filed on Dec. 28, 2018, now Pat. No. 11,132,479.

(60) Provisional application No. 62/750,012, filed on Oct. 24, 2018, provisional application No. 62/612,181, filed on Dec. 29, 2017.

(51) Int. Cl.
*B29C 70/38* (2006.01)
*B29K 307/04* (2006.01)
*B29K 63/00* (2006.01)

(52) U.S. Cl.
CPC ........ *B29C 70/386* (2013.01); *B29K 2063/00* (2013.01); *B29K 2307/04* (2013.01)

(58) Field of Classification Search
CPC ... B29C 70/386; B29C 70/54; B29K 2063/00; B29K 2307/04; G01N 2021/8472; G01N 2033/0003; G01N 21/88
See application file for complete search history.

(56) References Cited

U.S. PATENT DOCUMENTS

| | | | |
|---|---|---|---|
| 2016/0325490 A1* | 11/2016 | Safai | B29C 35/0261 |
| 2017/0052070 A1* | 2/2017 | Marsh | G01N 25/72 |
| 2017/0113422 A1* | 4/2017 | Maass | B29C 70/386 |
| 2018/0088063 A1* | 3/2018 | Glynn | G01N 25/72 |
| 2019/0003983 A1* | 1/2019 | Al-Omari | G01N 21/8851 |
| 2019/0061282 A1* | 2/2019 | Johnson | B29C 35/0805 |
| 2019/0300205 A1* | 10/2019 | Georgeson | G01N 25/72 |
| 2019/0318444 A1* | 10/2019 | Juarez | G06T 7/90 |
| 2020/0283171 A1* | 9/2020 | Holmes | G01N 25/72 |
| 2020/0340802 A1* | 10/2020 | Tyson, II | B64F 5/60 |

* cited by examiner

*Primary Examiner* — Deoram Persaud
(74) *Attorney, Agent, or Firm* — Bonini IP Law, LLC; Frank J. Bonini, Jr.

(57) ABSTRACT

A method and system for determining the quality and configuration of a structure that is constructed from a thermoformable material, such as a thermoplastic or thermoset material, and in particular thermoplastic composite tapes, where heat is applied to cure the thermoformable material. The quality of the build is monitored during the construction of the structure by determining the differential heat flux in the material as it cools from its elevated temperature. The system and method also may determine the location of defects in a structure being constructed so that remedial measures may be taken or production operations halted to address the defect. A transient thermal effect is applied to the structure being monitored, such as the thermoformable material being applied, which may be implemented from the applied heating of the thermoformable construction application process or additional heating.

27 Claims, 9 Drawing Sheets
(7 of 9 Drawing Sheet(s) Filed in Color)

Figure 1 - Laser Line in-situ data showing the real-time Gap measurement between the current thermoplastic strip verses the pervious strip on left. The data also shows the variation of compaction, as height across the tape verses the base material.

Figure 2 - Laser Line In-situ data showing the real-time Bridging of one tape strip onto a previous tape strip on right.

IN-SITU MONITORING OF THERMOFORMABLE COMPOSITES

CROSS-REFERENCE TO RELATED APPLICATIONS

This application is a continuation-in-part of U.S. patent application Ser. No. 16/236,081, filed on Dec. 28, 2018, and of U.S. patent application Ser. No. 16/236,072, filed on Dec. 28, 2018, and claims the benefit to U.S. Provisional Application 62/750,012, filed on Oct. 24, 2018, and U.S. Provisional Application 62/612,181, filed on Dec. 29, 2017; the entire contents of the aforementioned applications of which are incorporated herein by reference.

BACKGROUND OF THE INVENTION

1. Field of the Invention

The present invention relates to the field of composite structures, in particular thermoformable materials, such as thermoplastic, thermoset and metallic composite materials, and more particularly to monitoring the quality and configuration of a structure as the structure is being built. The invention further relates to additive manufacturing processes and devices.

2. Brief Description of the Related Art

Manufacturing in-situ monitoring is quite broad, but a new manufacturing technology is developing which is Robotic Thermoplastic Composite Tape Layup. Thermoplastic Composite Tape is a thermoplastic composite matrix with imbedded fibers.

Substantial manufacturing currently uses Graphite/Epoxy thermoset composites. Traditional tape layup with Graphite/Epoxy thermoset composite tape requires a tool at about 200° F. to wrap the tape on, vacuum bagging to suck out any entrapped air (debulking), and then putting the entire part and tool into an autoclave at high temperature and pressure to cure it rigid. When complete, the part is then removed from the tool. Non-Destructive Testing (NDT; typically ultrasonics, thermography, x-ray) is typically used after cure to determine the quality of the part, on an accept/reject basis. Repair, however, is difficult, as the structure has been cured, and is not readily reconstructed. In many instances, it is not even possible to repair the part.

Thermoplastic Composite Tape Layup uses a tape of thermoplastic (ex: nylon) with embedded fibers, laid at about 750° F. Currently, this very high heat is precisely applied using a laser and/or a heat lamp, and other methods. This material may be laid using a tool, or without a tool (tool-less), because it is cured in real-time as it is cooled. The savings are considered to be immense. Tools provide rigid structure for the building of the part, but can be very expensive. Tool-less manufacturing is the future, where two robots build against each other. Not only are there no tools, no autoclaves or other operations, this manufacturing of composite structures may be done anywhere, even in the field, or in space. Structural strength matches thermosets. Repair is easy.

However, because there is no tooling, a need therefore exists to confirm that what is being built conforms to the quality and shape of the intended structure, preferably as determined by the CAD design, for example, where the structure is being constructed in accordance with a CAD).

SUMMARY OF THE INVENTION

A method and system for determining the quality and configuration of a structure, which preferably is a structure that is constructed with the use or application of heat, such as, for example, to cure the material used to form the structure or a structural portion comprised of such a material. The present method and system may be used in conjunction with the construction of products from materials that have thermoformable properties, and preferably thermoplastic composite materials, and thermoset materials.

According to some preferred implementations, the method and devices involve constructing a structure using thermoformable materials, such as, for example, thermoplastic, thermoset or metallic composite materials. The method and devices are useful in conjunction with additive manufacturing, and may be used as part of an additive manufacturing process, to determine defects and/or potential defects as the manufacturing process is being carried out, or before one or more steps are carried out. The method and devices may be used as the composite material is being laid up, or alternatively, may be used after one or more materials, a number of toes or layers have been laid up so as to determine whether the subsequent layup or layering of material, e.g., through additional pressure or heat, or other manipulation, has resolved any previously identified defect or condition that may have been observed during the initial layup of a course or toe. The method and devices also may be used for quality monitoring of a completed structure.

According to preferred embodiments, material comprising the structure or component being applied or assembled to the structure, may comprise a thermoplastic material (material that is pliable when heated and solidifies when cooled, and may be reheated and reshaped), and in some other embodiments, the material may comprise a thermoset material (where heat is applied to cure the material into a form that cannot be melted or reshaped). The method and system may be used to determine the quality of a build, where the structure is formed from a composite layup. The composite layup may employ engineered materials composed of a matrix material (e.g. polyester or epoxy resins) and a reinforcing material (e.g. carbon fiber, glass mat or woven fabric). The composite layup may be applicable to both thermosets and thermoplastics, and according to preferred embodiments, a composite layup may be implemented using a tool-less thermoplastic construction.

According to a preferred embodiment, the method and system are designed to detect the presence of a defect in a structure, while the structure is being built. Identifying an out of tolerance condition, or other defect during the build process (e.g., the presence of an artifact or debris, or the misalignment of materials), may save time and resources (including costs), by permitting the structural defect to be corrected at the time the structure is being built, and preferably, before additional manufacturing steps are carried out (or a subsequent step that may make it impossible to remediate the defect condition). In such latter situations, the structure, when constructed having a defect, may need to be scrapped, and may not be able to be remediated. Identification of even a non-remedial defect during construction may still save costs and promote efficiencies throughout the manufacturing process, including those costs and efforts associated with one or more subsequent manufacturing steps (which may not therefore be carried out). The present system and method enable detection of defects that may arise during the construction of a structure, and in particular, where the structure is built from a composite material, and more particularly a thermoformable material, such as, for example, a thermoplastic composite (e.g., tape) or thermoset.

The method and system may be implemented using a robotic method for composite placement. For example the method and system may be employed in conjunction with robotic composite placement methods and equipment. One example of a robotic composite placement method is Automated Fiber Placement (AFP), and another example is Automated Tape Layup (ATL). In the former placement method, the placement of a fiber material, such as a fiber tape (e.g., continuous fiber tape) carried out using an automated machine, such as a robot, which lays each layer (or ply). The AFT procedure typically automates composites manufacturing process, which includes paying the tape, as well as applying heat. Some AFP processes may include automated procedures that involve heating and compacting resin pre-impregnated non-metallic fibers on a surface structure, or on typically complex tooling mandrels. The fiber may be supplied in the form of a bundle of carbon fibers impregnated with epoxy resin, commonly referred to as "tows". According to some applications, a "tow" may be typically approximately 0.500 in wide by 0.005 in thick and may come on a spool.

The latter Automated Tape Layup (ATL) procedures are typically used in the construction of aircraft parts, including aircraft wing skins and fuselages. The ATL procedure may involve laying one or several layers of composite tape, such as, for example, carbon fiber tape (or tows) onto a mold to create a part or structure. Automated machinery, such as robots, is used to guide the tape to the proper position.

According to some other implementations, the AFP involves a placement of one layer of material on top of another, which may be repeated for subsequent layers until the build of that part or portion is completed. For example, where carbon fiber material layers are used, they may be taken from a cold storage and placed onto a form or onto a designated area. The placement may be on top of another carbon fiber sheet or layer, and as the layers are now removed from cold storage (often freezing temperatures), they elevate in temperature and begin to adhere to the adjacent layer. The implementation of the present Thermography Cool NDE (TcNDE) devices and methods facilitate discovery of potential defects that may be present, which, is discovered later, when multiple layers of the composite are already formed together (even if before autoclaving or other treatment step), would render it not possible to remedy the defect (or would involve the waste of the entire multiple sheet composite. The present method involves tracking the layer or composite placed down as the cool stream of air (or other gas) is jetted over the surface of the layer or structure. If for example, a piece of a glove or other foreign object (debris) is present, the location where it is (such as between two adjacent layers), will react differently to the warming of the layers when they are subjected to the cooling air and are returning to a higher temperature from the cooled temperature (from the exposure to the cooling air). The device preferably is configured to robotically apply the cool air stream and thermographically record the structure, which preferably, is slightly trailing the cooling stream of air. A tracking camera, such as for example, an ARAMIS 3d tracking stereo camera, tracks the robotic head, which preferably includes the thermographic camera and the cooling head, and identifies the robot head with a coordinate in space so that the location of the robotic head and the location of the structure, and the area that the thermal imaging camera is imaging is known and identified. The potential defect or structural areas are therefore pinpointed and associated with the corresponding thermographic information for that location. The method and devices therefore may save considerable amounts of time (of the individuals involved in the construction) and conserve resources (materials used), which also in turn conserves energy and environmental resources. Moreover, the product or purpose for which the layers of material are being formed, also will benefit from either knowing the extent of a defect, or knowing that if there is a defect it is within tolerances or limits, or alternatively, knowing that a defect is present and that the defective product has not been used (has been scrapped, and preferably early on in the process).

Embodiments and implementations of the devices and methods also may be utilized with the implementation of UV imaging to determine quality during the build. The UV imaging may be utilized to determine the crystallinity of the structure being formed, and in particular, the crystallinity of the thermoplastic. The method is carried out utilizing a UV light source that is directed toward the structure or portion of the structure or thermoplastic component, and is viewed using an imaging component, such as a camera with an image sensor capable of recording the UV directed light and the response of the subject being monitored or measured. According to some embodiments, the UV imaging may be carried out in conjunction with the method and utilizing the devices to verify the quality of a completed structure, as well.

However, often during these manufacturing processes, in both AFP and ATL procedures, the composites are subjected to heat, which is elevated temperatures, which may be a couple hundred degrees (for thermoset materials), and several hundred degrees or more, for thermoplastic material (e.g., such as thermoplastic composites). The heating of the structure and/or materials used to form the structure (e.g., composites) is typically followed by a cooling phase. The cooling phase may take place due to the removal of the heat source (or according to other embodiments, there may be an application of a cooling source).

The composite structures, including aircraft skins and fuselages, may involve multiple layering of the composite material, which involves heating and curing of the composite material as it is placed into position. The present method and system are configured to track the quality of the build as the structure is being constructed. The present method and system image a field of view while the thermoformable material is being laid up and cured.

According to preferred embodiments, the present method and system may employ an imaging component that follows the robot and/or heads laying the material (such as composite tapes), and preferably the imaging component is configured to be carried (e.g., mounted) on the robot head so that the imaging has access to the visibility of the material, such as the tape, as it is being laid into position, heated, and cooled. According to some embodiments, the imaging system comprises a thermal imaging component, which may comprise a thermal camera (thermal imaging sensor coupled with an electronics linkage to circuitry or a computer that may receive and process the data). According to some preferred embodiments, the imaging sensor or camera is an infrared sensor (camera).

According to some embodiments, the method may be carried out by applying heat from an additional heating source (other than the one used for the production (curing) of the structure). For example, if a head cools the freshly laid composites so that the transient thermal effect is gone, additional heating may be supplied. According to some embodiments, the additional heating may be built into or supplied as part of the head to provide a transient thermal effect so as to enable the detection of the desired defects. In conjunction with the additional heating, according to some embodiments, the system may include a heat generator to provide additional heat for the imaging. The additional heating may be applied using thermal pulses or continuous heating. The additional heating source may be utilized, where, for example, the curing temperature of the material being applied is not sufficiently high enough to provide suitable degrees of variations in the structure when monitored. One example is where a thermoset material is elevated to 200 degrees but rapidly cools after the heat source used to cure the material is removed. Another example is where the material such as a thermoplastic composite is heated significantly to a few to several hundred degrees, but is rapidly cooled, or cools rapidly, so that additional heating is needed for the detection being carried out. The additional heating source may be provided in conjunction with the head and/or imaging component or may be separately provided, and preferably is arranged to be directed at the location where the robot has just laid the tape or material and where the heat was removed. This additional heating may be pulsed heating or direct heating (e.g. for a timed duration, or administered with the passing robot head), so as to aid the imaging system and method to detect potential conditions or defects in the structure, as the structure is being formed, and before the structure is completely built.

According to alternate embodiments of the invention, in situ monitoring of composites may be carried out by Thermography Cool NDE (TcNDE). The monitoring of the structure being constructed, such as a thermoformable material, e.g., thermoplastic and thermoset, may be carried out using TcNDE. According to some implementations, while the Thermography NDT has been described in connection with applied or other radiant thermal heating, (e.g., using the heat applied to form the structure, or applying heat via another source such as a halogen or xenon lamp), which heats an area of interest while the thermography statically watches the area cool. According to alternate embodiments that employ the Thermography Cool NDE (TcNDE), convective cooling is used to thermally stress the part, thereby drawing out the ambient heat. The thermography imaging is used to measure the warming of the area is imaged to record the thermal condition, and change. This may be done as discussed herein with manual or robotic means, and with an imaging head imaging the area of interest. According to preferred embodiments, a cool stream of air is applied to the structure or portion of interest (e.g., where the build or thermoformable material is being applied), and the imaging records the thermographic information, and in particular when the area is warming after the application of the cooling. The method implementations also may include repairing or reconstructing the structure that is being formed from the composites as it the structure is in the process of being built, and not yet completed. For example, the structure may still be at an elevated temperature, and in some instances, if there is a detected defect or condition, the tape may be removed from the defect location, and reapplied, or another tape applied. As discussed, the defect could be a piece of material that made its way between layers, a misaligned or out of alignment structure (e.g., tape course misaligned, uneven or insufficient curing), or other issue tending to render the structure unfit or out of tolerance. The defect or condition may be present in one small area or location, rather than being an entire course of tape or layer.

The system and method provide an alert that is generated when an abnormal condition is observed during the build through the thermal imaging. The alert may be sent to an operator or be observed by an operator, or may be tied into the operation of the automated machine, such as the robot, to prevent further construction of the structure (which may require a response from a human operator). Where a robot has the capability, the alert may guide or instruct the robot to remove the defective layer and reapply it, or to apply a new layer in its place (or in the proper place).

According to preferred embodiments, the method and system are provided for detecting defects and preventing defects in the ultimate structure. The present method and system may be implemented in conjunction with a structure constructed using a thermoset material, where the method and system identify defects prior to autoclaving the thermoset, and allow for the repair of a defect or irregular condition before the structure is set (i.e., through the autoclave or other applied heat).

The monitoring carried out using the present method and system has the capability to save costs by detecting defects and other potential conditions while the structure is in the process of being constructed, and before the structure is completed or fixed, where repair is not possible or may be too costly.

According to preferred embodiments, preferably, the method involves monitoring a thermoplastic composite structure, as the structure is being built.

The quality and configuration of the structure, according to preferred implementations, may involve the correspondence of the structure being built to the CAD file of the structure, as the structure is being built. According to some embodiments, the CAD file may include CAD coordinates, and, a quality of the structure build in process may be determined relative to its proximity to the CAD coordinates (and/or with any tolerances that may be acceptable).

The present method and system is useful where there is no tooling. The real-time in-situ monitoring provided by the present method and system is utilized to confirm quality and shape to CAD design. The present method and system may be implemented in conjunction with a three-dimensional (3-D) photogrammetry application, such as for example, an ARAMIS system (Gom GmbH). ARAMIS is a tool for carrying out 3D photogrammetry and DIC (Digital Image Correlation), and can measure the 3D coordinates of everything in an imaging FOV (Field-of-View), either using defined targets or DIC pattern(s). The pattern or patterns may comprise a projected pattern, or may comprise a pattern on the surface of an object or part being assembled. The method and system utilize Thermography In-situ Inspection (TII) or NDI (Non-Destructive Inspection), which preferably is carried out using an infrared camera. The method and system implement Thermography In-situ Inspection (TII) to image the differential heat flux. According to preferred embodiments, the differential is monitored with regard to the heat flux of the material as it cools, and according to some alternate embodiments the differential is a measurement of the heating as the structure or portion thereof after being cooled (e.g., warming to an ambient temperature). For example, the method may be used for in-situ thermoplastic composite structure, where the structure is constructed from a tape that may be installed by placement with a robotic head. The system and method determine the differential heat flux of the just laid tape cooling with the Thermography In-situ Inspection (TII) or NDI (Non-Destructive Inspection), which preferably is carried out using an infrared camera during the construction of the structure, to determine the differential heat flux of the just laid tape cooling. In addition, the structural locations are known, as the imaging takes place with the robot or capturing device being calibrated to the location of the structure. The present method and system pinpoint the location of the detected defect, so that not only is the quality of the structure indicated, but the precise location where the defect is observed also is identified. In addition, the thermographic differential in the heat flux, as the structure or component applied cools (e.g., cooling of the tape, or in the alternate embodiments warming from being cooled), is evaluated to determine the extent of the defect, and may even provide dimensions and degrees of the condition or imperfection detected.

According to preferred embodiments, the thermographic component, such as an infrared camera, typically is carried by or mounted to a robotic head. For example, the method and system may be implemented in conjunction with a robot that is involved in the construction of the structure. The robotic head may carry an imaging component, such as the infrared camera, and the method may include conducting real-time imaging of the just laid tape cooling, as the head moves on to further construct another portion of, or the remainder of, the structure. Where previously, after a composite structure is built, Thermography NDI uses thermal heating (pulsed or continuous) to detect voids, disbonds, porosity and other structural weaknesses in the thermoplastic structure, it is too late, and in many instances an entire structure or major portion of it, must be discarded.

In accordance with preferred implementations of the method and system, thermography equipment is used to capture and detect the thermal properties of the material, preferably during the process of the construction of the structure (e.g., while the thermoplastic composite material or thermoset material is being manipulated to produce a structure). According to preferred implementations, an ARAMIS thermography system may be used to capture thermographic information. ARAMIS Thermography couples ARAMIS 3D photogrammetry with Thermography NDI by calibrating the infrared camera with the ARAMIS photogrammetry cameras. This allows the Thermography NDI data to be known in 3D coordinates of the structure being measured. The system may include one or more robots, or robotic heads carrying a thermographic imaging component (e.g., an infrared camera), and preferably an illuminating source (infrared lighting). According to some embodiments, the system may employ photogrammetry tracking of the robots and/or structure, in real-time relative to the CAD (computer design). For example, the sensing head carrying the in-situ sensors or the robot head, or both, may be provided with photogrammetry targets thereon, enabling their respective locations relative to the structure being constructed (i.e., the build) to be in known continuously, in real-time, and in 6-DOF.

The present system and method may be implemented in conjunction with automated tape laying (ATL) and automated fiber placement (AFP) equipment to provide determinations of conditions, and, in particular, defects that may otherwise go unnoticed, or defects that may be identified during the construction process, before the structure is complete, and/or other instances, before the completion of a manufacturing step that may render the structure (or portion thereof that has been built up to that point) to be rendered unusable and have to be discarded.

According to some embodiments, the structure may be constructed using thermowelding to weld together one or more thermoformable materials. The thermowelding may apply a suitable heat from a heating source to form an article by joining together one or more parts or materials. The welding may be carried out by employing manual techniques or robotic or robotically assisted applications. The thermowelding may comprise joining one or more materials to form an article, or may join a material or materials to an existing component, frame or structure, in order to complete a step for or the formation of a structure, or in some instances the repair of a structure.

Preferred embodiments involve constructing a structure with a material that has thermal properties, and which may be used with an application of heating and/or cooling during the placement of the material onto the structure in the process of being built (e.g., to cure the structure).

According to a preferred implementation, a structure is built using a tape, preferably a composite tape. The composite tape is positioned to form the structure. Preferably, the tape is a thermoplastic composite tape, which is applied at an elevated temperature. According to some embodiments, the elevated temperature at which the tape is applied may be about 750 degrees F. The differential cool down of the elevated temperature laid tape is observed. The cool down is indicative of the quality of the material structural integrity. During cool down, strain is determined and material properties may be estimated, and manufacturing defects detected. According to some alternate implementations, the structure is cooled with an applied cooling procedure, such as via a directed cool gas stream or brushing of cooled gas on or over the surface or area of interest (e.g., the bond or build location), and the structural integrity is determined by monitoring and evaluating the thermographic imaging of the warm up as, the cooled structure warms from its cooled condition.

The methods for monitoring the quality of the build of a structure may be carried out in conjunction with a method for constructing a structure. The quality of the build may be determined, including whether there is appropriate gapping of overlapping, adjacent or spaced-apart layers. The quality determinations may take place as the structure is being built. For example, where layers of tape are being applied to produce a structure, the positioning of the tape layers may be monitored to ensure that the tape is being provided in the desired location, or that it is within any tolerance required by the manufacturing process. The methods and systems herein may also be used to make repairs to a structure.

These and other advantages are realized with the present invention.

BRIEF DESCRIPTION OF THE DRAWING FIGURES

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENTS

Figure 1:
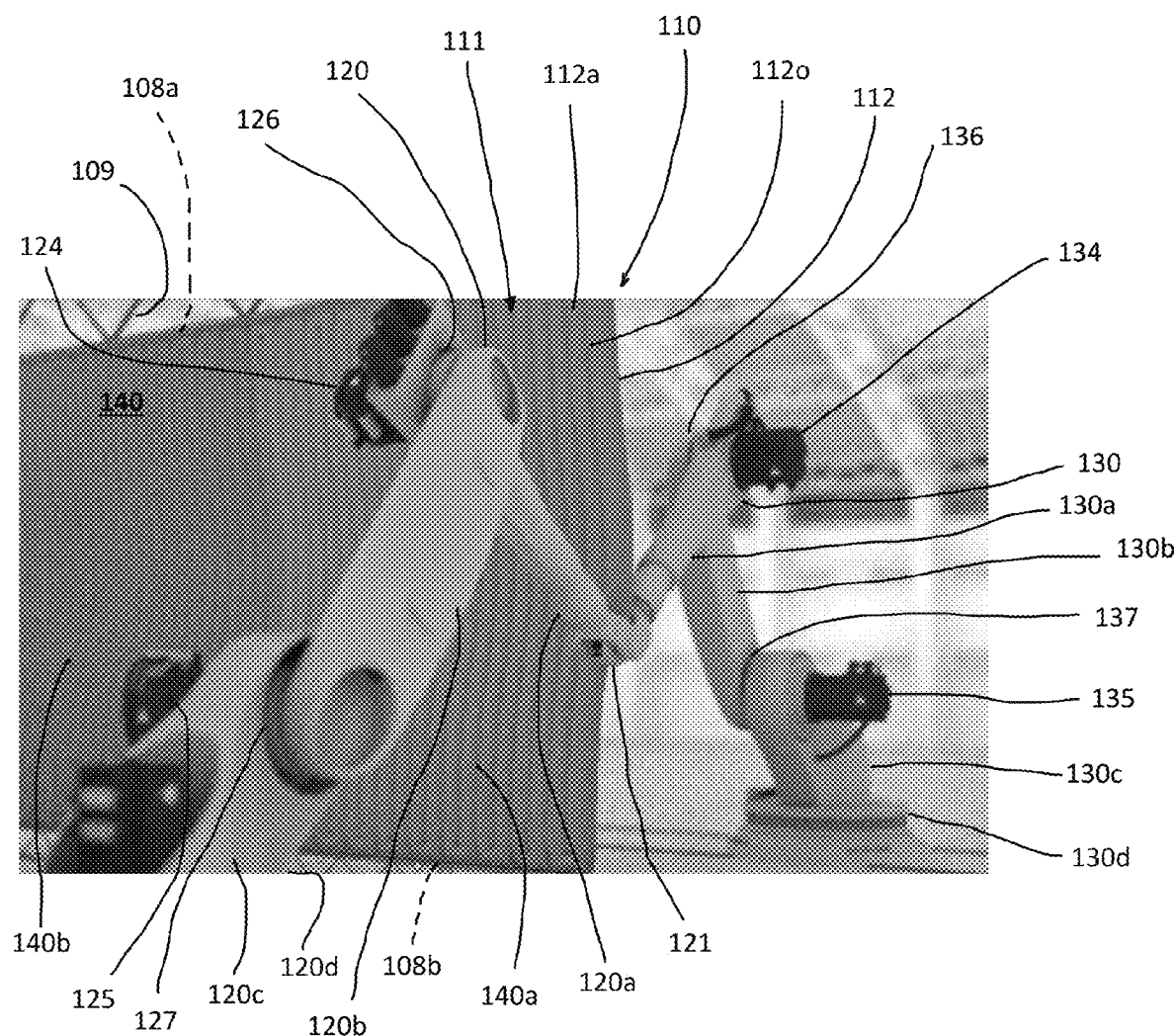
FIG. 1 is a perspective view of an illustration of a composite structure being constructed, where robots are used to lay up tapes.

A method and system for determining the quality and configuration of a structure that is being produced, while the structure is in the process of being built. Preferred embodiments of the process and apparatus used to construct the structure may involve a robot that is programmed to construct a structure (such as a land or air vehicle, e.g., aircraft, satellite or automobile, or other product) and in particular, using the application of a thermoformable material, such as a thermoplastic composite material or thermoset material.

As the structure is being constructed, the structure is monitored using thermographic techniques. According to a preferred implementation, the structure is monitored using thermography to determine a heat flux differential in the cooling of the structure, and in particular, for a component that is being applied to the structure, such as for example, a thermoformable material, which may comprise a thermoset or thermoplastic material.

According to a preferred embodiment, the structure is formed by the application of thermoplastic composite material, which may be in the form of a sheet or layer, such as a tape or tapes, which are positioned at designated locations of the structure (which is in the process of being built), and heated to thermoform the material (i.e., curing). For example, where the thermoplastic composite material (such as a thermoplastic composite tape) is used, preferably the process involves laying the tape in the designated location and rapidly heating the tape with the application of heat. The structure is constructed with the thermoformable materials and the use or application of heat, such as, for example, to cure the material used to form the structure or a structural portion comprised of such a material. The heating often is rapid heating that heats the materials, in the case of thermoplastic composite materials, from the ambient temperature of the working site location, to an elevated temperature, which according to some preferred embodiments, may be a few to several hundred degrees F. (e.g., 500 to 1000 degrees F.). In the case of some thermoset materials, the temperature may be lower, such as, about 200 degrees F.

According to a preferred implementation, one or more robots are configured with a material dispensing mechanism, preferably, a tape dispensing mechanism to dispense a tape from the robot onto the structure being built or at a designated location that is to form the structure being built or a part thereof. The robot has a heater that heats the tape as it is being applied to the location. The thermoplastic composite tape rapidly cools once the heat source is removed, which typically is while the tape is being positioned and applied to the structure. The robot continues to apply the tape, in adjacent, overlapping or partially overlapping, diagonally or in some other course, to complete the structure, or complete a portion of the structure.

During the application of the component to construct the structure the quality of the structure being constructed is monitored. In particular, the application of the thermoformable material, such as a thermoplastic composite tape, involves heating and cooling. The flux differential during cooling is monitored, while according to some alternate embodiments (e.g., TcNDE) the cooled structure is monitored for warming from its cooled condition or state. Preferred monitoring involves the use of a thermography apparatus which measures the heat of the structure during the build process. One example of thermography apparatus is an ARAMIS system (Gom, GmbH). According to preferred embodiments, the cooling is observed by the cooling of the thermoplastic material when the heat from the heat source is removed and the thermoplastic material is applied to the structure. The robot preferably carries a thermographic imaging system, including a thermographic camera (image sensor), which may comprise an infrared camera, and according to some embodiments may include an infrared illumination source to pulse or continuously illuminate an area with infrared light in order to capture the differentials that may identify defects or conditions in the structure or material that is being applied or has been applied.

According to some TcNDE embodiments, a cooling source may be provided or carried on a robot.

In some productions, completed structures may have had areas of concern detected during In-situ Inspections, and the inspection and monitoring during the build may direct particular focus on such areas. Thermography NDI (Non-Destructive Inspection) may be used to detect voids, disbonds, porosity and other structural weaknesses in the thermoplastic structure. Pulsed Thermography NDT (Non-Destructive Testing) may be carried out by putting a thermal pulse into the material surface over a large area. An imaging component, such as an infrared camera, images the surface while the pulse enters and is absorbed by the material. Defects may cause thermal transmission resistance, causing defects to remain hotter than the surrounding material. The time verses temperature variance determines depth of the defect in the structure. According to preferred implementations, Thermography NDT (e.g., using the ARAMIS system, ARAMIS Thermography NDT) allows the Thermography NDI image to be known in 3D coordinates of the structure being measured. This allows the defects detected to be accurately sized and located in the structure. The system and method may be used in conjunction with the augmented reality system for component assembly and archival baseline clone, shown and described in my co-pending U.S. patent application Ser. No. 16/236,072, filed on Dec. 28, 2018, and U.S. provisional application No. 62/612,181, filed on Dec. 29, 2017, the complete contents of those patent applications of which are herein incorporated by reference.

According to some embodiments, a sensing or monitoring head may be provided to follow the build as a structure is being constructed. The sensing or monitoring head may include imaging components, such as an infrared camera, as well as a heating or lighting source to provide heating to a structure in the event that the heat from the thermoforming procedure would dissipate too rapidly for the thermographic image capture to obtain suitable information. The additional heating may be supplied in the form of an infrared light source, pulsed or continuous, which is directed at the location of interest (the location where the thermoformable material has been applied and/or a location or locations of concern). According to some alternate embodiments, the sensing and monitoring system (or head) may be provided as part of the automated machinery or devices that are used to carry out the build. For example, the robots (such as those depicted in FIGS. 1 and 2) may carry or be constructed with a sensing and monitoring head. The head is located to direct the imaging component, and any auxiliary heating source, to the build portion (such as the tape laying head) of the robot, and to follow the thermoformable material as it is placed into position (and heated with the robot or machine application of heat). The sensing and monitoring head preferably follows the structural additions of the thermoformable material, and as the material cools from its rapid heating, collects the information (e.g., such as thermographic information from the infrared sensor or eddy current sensor). The information is then processed to determine whether there is any differential in the heat of cooling that may signify the presence of a defect or other abnormal condition (e.g., out of alignment placed material). The system may be included in automated structures, or may be separately provided for use with automated structures. According to some embodiments, the system also may be used in conjunction with hand layup applications, to follow the layup of thermoformable materials (e.g., tapes and fibers). For example, the imaging component may be positioned to capture the components being laid up by hand, and in some embodiments may be configured to follow the material as it is laid into position and cured.

Referring to FIG. 1, an example of a robotic system 110 is depicted, shown carrying out the construction of a structure 111 using a thermoplastic composite tape 112. The system 110 is shown including a tape laying robot 120 which includes a tape laying head 121. A second robot 130 is shown and provides a following surface against which the first robot 120 may lay the tape 112. As shown in the example, the structure 111 is comprised of a number of courses of tapes 112, which are adjacently arranged, and slightly overlapping (the overlap being represented by reference 112*o*) with a previous adjacent tape 112*a* (along an edge thereof, 112*o*). The structure 111 also includes a frame portion 109 which may serve as a support onto which the tape courses 112 are applied. One or more additional support members, such as the supports 108*a*, 108*b*, may be provided to support the tape 112. According to some constructions, the frame or supports may comprise part of the structure being formed, while according to other embodiments, there may be temporary supports or frames on which the thermoplastic structures are formed. The tape laying head 121 of the first robot 120 preferably includes a heat source to heat the tape 112 while the tape is being applied. The first robot 120 and second robot 130 preferably are constructed to operate using 6 DOF (degrees of freedom), so that the robots 120, 130 may move to any suitable position to apply the tape 112. The tapes 112 are shown forming a panel 140. The panel 140 is shown having an illuminated portion 140*a*, and a portion that is not illuminated 140*b*. The illuminated portion 140*a* indicates where the potential imaging area is located. The first robot 120 preferably may carry an imaging component, such as a camera, or alternatively, a camera may be situated on another support so that the field of view includes the area or portion of the structure being monitored. A robot, such as the first robot 120, may carry an illumination source to illuminate an area with pulsed illumination, and preferably the source comprises an infrared illumination source (infrared light source). The light source preferably is directed at the location of the robot head 121 where the tape is being dispensed to form the structure, and according to some other embodiments, an illumination source may be adjustable (e.g., in terms of its direction and intensity, and breadth or scope of coverage) to be controlled to illuminate a desired location (e.g., location of interest, location of inspection).

In the exemplary depiction of FIG. 1, the robots 120, 130 are each shown having a plurality of arms, such as the arms 120*a*, 120*b*, 120*c* of the first robot, and arms 130*a*, 130*b*, 130*c* of the second robot 130, and a base 120*d*, 130*d*, respectively. A plurality of operators, such as the motors 124, 125 of the first robot, are provided to control the movement of the robot arms 120*a*, 120*b*, respectively, and, motors 134, 135 of the first robot, are provided to control the movement of the robot arms 130*a*, 130*b*, respectively. The robot arms also may tilt and move in a radial or spherical direction, as the arms preferably connect at connection ports 126, 127 and 136, 137, which may function like a socket joint. Each lower arm 120*c* and 130*c* preferably may pivot relative to its respective base 120*d*, 130*d*. The system 110 is one exemplary depiction of a thermoformable operation, where a thermoformable material, represented as the thermoplastic composite tape, is being applied to construct a structure. In addition to the exemplary robots and automation arrangements illustrated, the present method and system may be employed in conjunction with devices, including other robots and robot arrangements.

Figure 2:
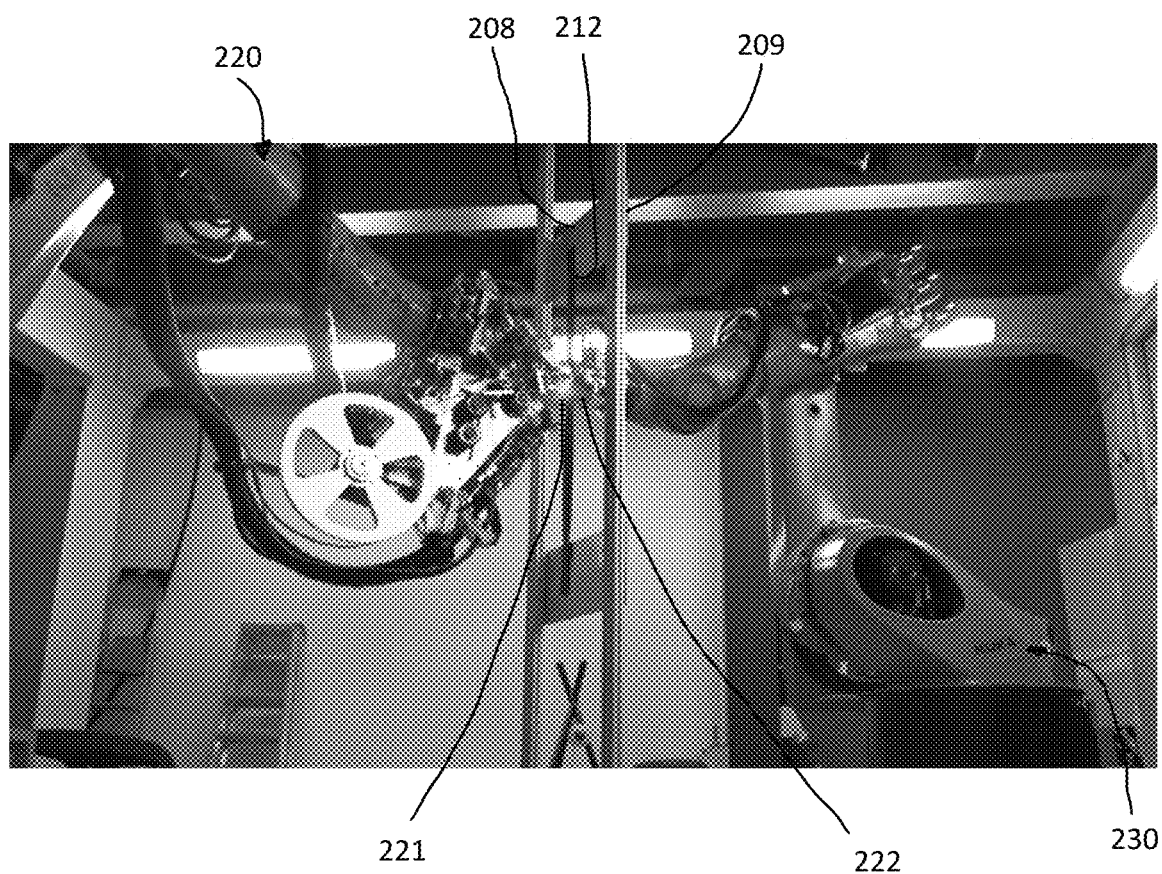
FIG. 2 is another perspective view of robots carrying out tool-less manufacturing, showing dual opposing robots laying thermoplastic tape.

FIG. 2 is another exemplary depiction of robots 220, 230 carrying out tool-less manufacturing, showing dual opposing robots 220, 230 laying thermoplastic tape 212. The first robot 220 includes a tape laying head 221, which includes a heating device 222 directed to heat the tape as the tape is laid into position on the structure 208 supported by the frame 209. The second robot 230 provides a back surface against which the first robot 220 may lay the tape 212. The robots 220, 230 shown in FIG. 2 may operate similar to the robots 120, 130 depicted in FIG. 1 and described herein.

A computer or other processing device, containing software and including a memory, may be utilized to direct the movements of the robots or other application device that applies the thermoformable material, such as the thermoplastic composite tape to form a structure. The computer may be programmed with instructions for constructing the structure by positioning the component, such as the tape, in a designated position (such as the overlapping of an adjacent layer as illustrated in FIG. 1).

A computer or processing device preferably is used to process the imaging information captured by the imaging component in order to determine the thermal differential that may be present in a structure being constructed when the cooling of the applied thermoformable material takes place (which is usually after the rapid heating to cure or form the material). The imaging information is transmitted from a sensor (e.g., such as a camera imaging sensor), which preferably comprises an infrared sensor, that is electronically coupled to the computing device. The imaging information obtained by the sensor is stored and processed to determine the indication of the heat absorbance that is associated with the component applied to the structure (e.g., tape), and any location or locations that are determined to be different than that of the surrounding area. Detection is carried out as the component applied. The detection may take place for example, where a thermoplastic composite tape cools from an elevated temperature to a lower temperature (the elevated temperature being a few to several hundred degrees). This cooling may take place after the thermoformable material is cured with heat (or after being heated to effect a transient heating effect therein, e.g., with a pulse application of heat), and heat is absorbed by the material, such as the structure and tape applied to the structure. Thermal transmission resistance is a property that may be measured using the thermal imaging. For example, defects may cause thermal transmission resistance, causing those locations where the defects are present (i.e., the defects) to remain hotter than the surrounding material (and cooler than the surrounding material in the case of TcNDE, e.g., exhibiting a reduced rate of warming). The level of defect, such as the depth of the defect in the structure, also may be determined based on the time versus temperature variance. Other defects also may reveal thermal imaging patterns that indicate their presence, such as debris inadvertently present between a layer, disbonding of the tape, or other condition. According to preferred embodiments, the system may be programmed with thresholds that indicate levels of heating differentials that when detected generate an alert condition. According to some preferred embodiments, the differential condition detected also is mapped to the structure location using the RVAT system and/or CAD of the structure (or the as-build structure CAD).

According to preferred embodiments, the imaging information is processed to determine whether a defect is present. Preferably, the determinations are carried out during the construction of the structure. Referring to FIG. 1, as the robots 120, 130 construct the structure 111 by applying courses of thermoplastic composite tape 112, the construction is monitored using thermography, and a computer or processor processes the thermal information captured by the sensor, as the structure is being constructed. Preferably, the imaging takes place throughout the entire build and of each surface that is constructed. The thermographic image is processed as the structure is being constructed, and the image information of the structure surface is monitored for differentials in heat flux that correspond with a defect or other monitored condition. The software is configured with instructions that process the information, and when a defect is detected, an alert may be generated. This may be in a form that appears on a display, a sound, a message or other means for informing the appropriate human operator, or machine. According to some embodiments, the process automation may be configured to cease further construction operations when a defect is detected. For example, where a defect is detected in a construction operation, the component addition, such as the tape application, may be halted until the condition is addressed or resolved. Where a defect condition is detected in a tape (e.g., disbonding), the tape may be removed from the structure being built and replaced. This detection mechanism therefore may prevent the structure from being completed with the defect, which may otherwise render the structure unusable or scrap, if it were otherwise to be completed with the defect present. The monitoring of the structure being built also may provide information that an operator may view. In addition to the processing of the detections, an operator may view the imaged structure and the imaged courses of components (such as the tape), during, and even after the structure has been completed.

The system may include programming to react to the level and extent, or type of defect detected. For example, where a defect is detected at a particular location or structure that is present but within a tolerance, the construction of the structure may be permitted to continue, while a defect that is present and is larger in degree or present at a critical location of the structure may cause the construction operation to cease until the condition is addressed or remedied. According to some embodiments, the automation equipment, such as a robot, may be configured to carry out remedial operations when a defect is detected. One example, is for the robot to remove the tape that has been applied, and re-apply the tape (or a new course thereof). This may be useful where the robot is carrying out construction operations distant or remote from human operators.

Figure 3:
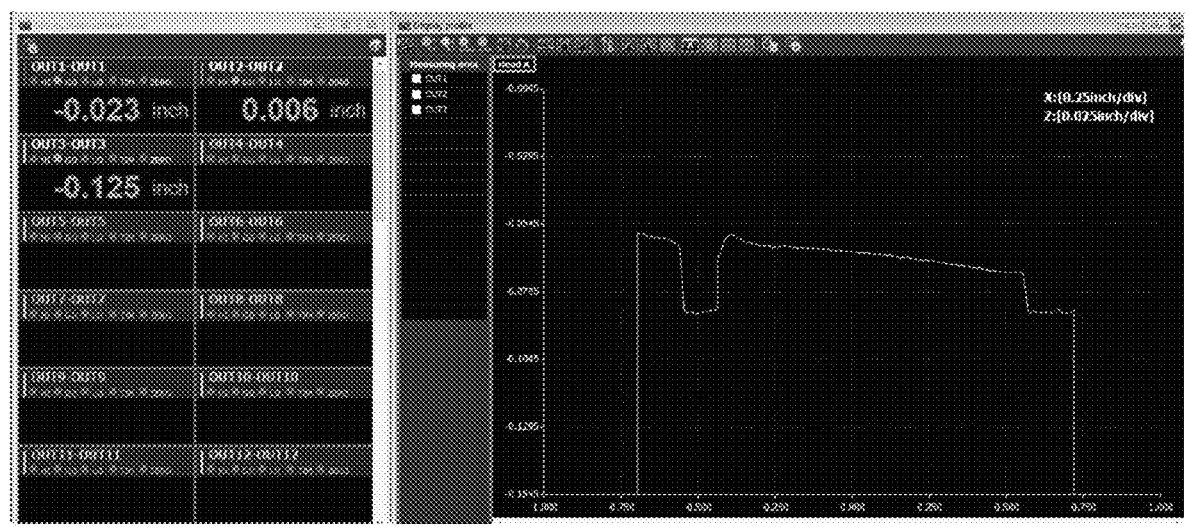
FIG. 3 is a an exemplary depiction of a computer screen showing laser line in-situ data for a thermoplastic strip versus a previous thermoplastic strip.

As illustrated in FIG. 3, Laser Line in-situ data showing the real-time gap measurement between the current thermoplastic strip verses the pervious strip on left. The data also shows the variation of compaction, as height across the tape verses the base material. In the depiction of FIG. 3, the real-time GAP measurement is within tolerances. In addition, the variation of compaction also is being monitored, and, as represented in FIG. 3, is the height across the tape versus the base material. The compaction variation represented by the graph in FIG. 3, is within tolerances. FIG. 3 illustrates an example of the method for monitoring the construction of a structure being used in conjunction with a structure being constructed from a thermoplastic composite tape material. The method is used to monitor the in-situ build process, and monitors the compaction variation as the structure is being built, which, in the example illustrated in FIG. 3, is a composite structure being formed by laying thermoplastic tape. The variations enable detection of the defect or out of tolerance parameter, and identification and alerting of the condition.

Figure 4:
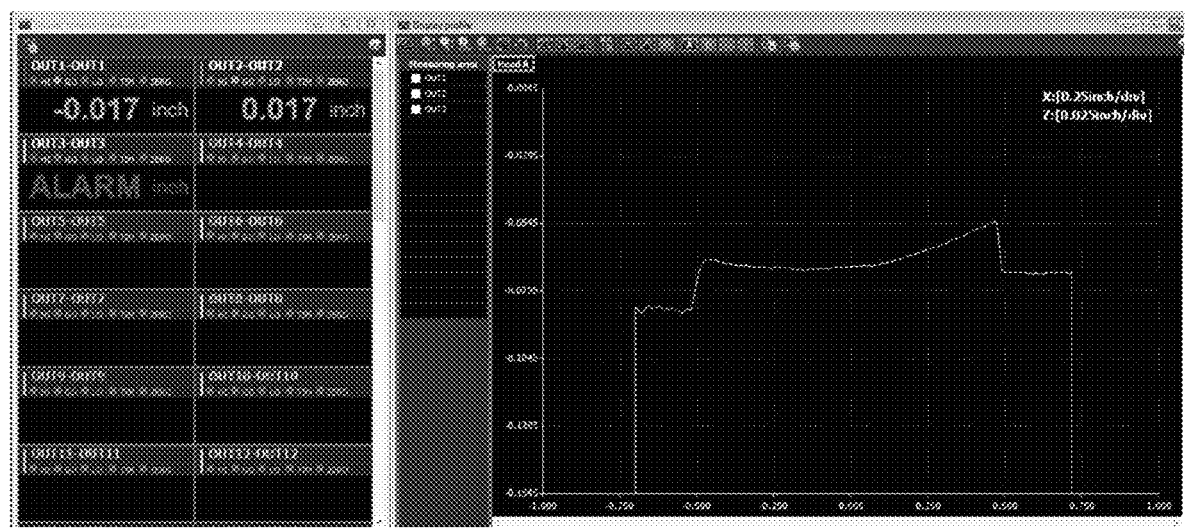
FIG. 4 is a an example of a computer screen display showing laser line in-situ data for a thermoplastic strip versus a previous thermoplastic strip, where a defect condition is detected.

Referring to FIG. 4, the Laser Line In-situ data shows the real-time bridging of one tape strip onto a previous tape strip on the right. In FIG. 4, there is an out of tolerance condition, and, as is depicted on the left screen window, there is an "Alarm" condition, as the system detects that the tape build does not contain the next tape layer in the appropriate position. The tape layer is being monitored as it is being laid, and the determination of the tape layer location as well as other aspects of the build quality, such as whether there is a lack of adhesion, an errant particle between the layers, or other problem or condition, is determined as the structure is being constructed.

The method and system preferably implement thermography in-situ inspection. In the case where the structure is being produced from a thermoplastic composite tape, heat is applied, often at very high temperatures, to heat the tape to an elevated temperature. The composite tape may be a few hundred degrees up to 750 degrees (or more), and immediately after the heat is applied, the tape beings to cool down. During the layup of the thermoplastic composite tape at an elevated temperature (e.g., about 750° F.), the differential cool down is observed. The cool down is indicative of the quality of the material structural integrity. The method and system implement a laser line In-Situ Placement Verification (ISPV) to determine the quality of the structure being built, and whether the tape layer is where it needs to be. The robot head, such as the robot head 120*a* shown in FIG. 1, is programmed to lay the strips of thermoplastic tape, and preferably may lay them in a spaced arrangement, e.g., spaced from each adjacent tape. In the exemplary depiction illustrated in FIG. 1, during layup of the thermoplastic composite tape, the robot head tries to lay the next strip of tape, 0.020 inches from the previous strip. In-situ placement verification is utilized to confirm this gap. FIGS. 3 and 4 represent the computer screen displaying the information and monitored representations of the in-situ build. If the real-time monitoring of the gap is getting larger, the robotic head that is laying the tape (e.g., such as the head 120*a* of FIG. 1) can be guided back to the correct gapping. If the real-time monitoring of the gap is getting smaller, then in order to prevent bridging onto the previous strip, the head may be guided back to the correct gapping. The In-situ Placement Verification (ISPV) with the Laser Line can also measure compaction of the material in real-time by measuring the tape verses the base material on either side. The guiding of the robotic head back to a position where it provides the correct gapping may be done automatically as a function of the detected tape gapping or tape positioning. The image data determines whether a gap is present, and if it is present, then sends an instruction to the robot motors or controller to reposition the robot head. The monitoring may continue as the robot head is adjusted so further adjustments can be made, or to verify completion of the adjustments (to the correct position).

The method and system may monitor the as-built structure and thermoformable material to determine the height of the materials, such as for example, the thermoplastic tape being applied to produce the structure. According to preferred embodiments, laser profilometry is carried out to provide the real-time non-contact measurement of the height of materials in the manufacturing processes that take place. As is depicted in FIGS. 3 and 4, there is demonstrated, screen displays representing the measurement of gaps and laps. As depicted in FIG. 3, there is illustrated the profilometry of a gap, and in FIG. 4, the profilometry of a lap). According to preferred embodiments, the system may include a compact in-situ sensor on the robot. Preferably, the sensor is located on the robot AFP/ATL head. The sensor is directed and configured to follow the layup of the thermoformable material (such as a thermoplastic composite tape). The robot head (see e.g., FIGS. 1 and 2), according to preferred embodiments, houses a laser profilometer, a thermography camera, and optionally also may include eddy current probes. The laser profilometry will provide height measurement across the applied toes or tape, for continuous, real-time measurement of gap, lapping and twists. The system may store this data, or may process the data and just use it for alarm of real-time out-of-specification build, or may use it for a present remedial operation.

Figure 5:
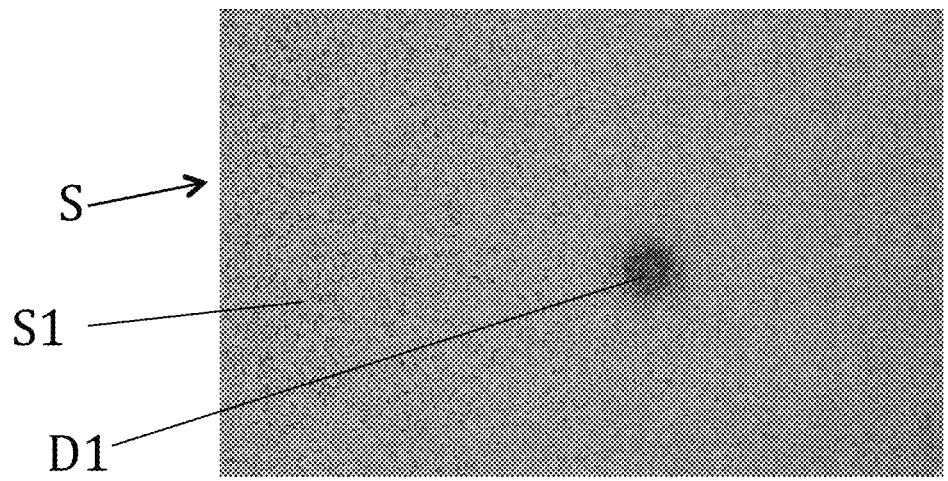
FIG. 5 is a thermography image representing a structure that contains a defect.

Thermography NDT is a primary technique for bond quality and disbond detection. As illustrated in FIG. 5, a thermographic depiction of a structure is represented, and shows a thermography delamination measurement. The thermographic depiction illustrates colors that correspond with different heats on the surface of the structure. As is illustrated, the structure S is shown, and, in the image of FIG. 5, represents a portion of the structure, the portion of interest, which, preferably is the portion where the thermoformable material has been recently deposited or laid. A first area of the structure S1, is represented by a first thermographic image color of the color gradient (which is blue, denoting a cool area). A second image color of the color gradient is identified as D1. This image area D1 is a location on the structure that is red or warm, and in the image of FIG. 5 identifies a defect. The illustration in FIG. 5 represents a typical indication of a defect condition, such as in the example illustrated, a delamination in graphite epoxy. As also discussed herein, the defect location and locations of areas that do not contain indications of defects, are identified in relation to the structure, including a structure that is being constructed at the time of the imaging. The system and method may utilize an imaging system, such as the ARAMIS system, and the CAD of the structure being constructed (or the CAD of the structure as it is being constructed), to pinpoint the location of the defects. The location of the defect identified on the structure may be identified by CAD coordinates (x,y,z coordinates) for storage or processing, or for further instructions to a human or to a robot or automatic processing machine (e.g., ATL, AFP systems). The system and method may be used for detection of defects in hand layup of composites, as well as robotic layups and construction of thermoformable structures and articles. The system and method detect defects, including, for example, foreign object debris and/or foreign object damage (FOD). This may occur in robotic assemblies where tape is being laid (including ATL processes), and also in hand layup of composites.

For in-situ thermoplastic measurements an infrared camera (IR camera) is utilized as the imaging component to image the cooldown of the AFP toes or ATL tapes from their elevated placement temperatures (e.g., 750° F.) to near ambient during a build. During an AFP/ATL pass, the toe/tape will cool down across the sensor image, providing measurement of the thermal flow across the thermoplastic toes/tape, and providing a good measure of local bond quality. The system may process the thermal flow information and identify whether there are any abnormalities or areas of concern present. The system may conduct processing in the form of issuing and/or communicating an alert, stopping the automated process (AFP/ATL), or undertaking some other action (e.g., align the robot or automated machine). The processing of the image information may be carried out with a computer having a hardware processor and software stored on a storage component or media (e.g., hard drive, flash drive/memory, or chip), that contains instructions for capturing the thermal image information and processing the information to determine whether a defect is present, and preferably where the defect has been identified.

According to some preferred embodiments, the robotic head is controlled with software that processes the inputs from the ISPV, and makes a determination whether the structure build is taking place according to the proper parameters. In the present example, the robotic head is controlled with software that processes the inputs from the ISPV to determine whether the gap is suitable for the build. If the gap is straying, for example, getting too large or too small, then the program guides the robotic head to the correct gapping. The system continues monitoring of the tape and gap, and the ISPV may be continuously determined, so as to provide guidance to adjust the robotic head to the proper position.

According to preferred embodiments, an imaging system that monitors the positions of the robot, structure and/or components being applied to form the structure (such as an ARAMIS system) is utilized. According to preferred implementations, the ARAMIS system is used to track the robotic head in 6-DOF. During robotic layup of the thermoplastic composite structures, the robot head(s) try to precisely move in 6-DOF (Degrees of Freedom) to create the part being built and, according to some preferred embodiments, to precisely lay the tape right next to the previous strip. Complex multi-axis robotic operations have difficulty knowing precisely where they are. ARAMIS Tracking tracks the robot head with great precision relative to the real structure being built, so that the robotic head location is determined and identified relative to the structure being built.

The method and system also determine the quality of build in relation to the CAD design of the structure being built. ARAMIS Projected Net Shape Verification may be implemented to determine the verification of the part being built. According to some preferred implementations, as depicted in FIGS. 1 and 2, robotic layup of the thermoplastic composite structures preferably may be tool-less. In other embodiments, minimal tooling may be used (or other supports that may be temporarily provided, such as a frame, etc., or that may be part of the final structure). According to preferred implementations, the shape of part being built needs to be verified relative to CAD design. Complex structures may have thermal warpage, sag or other 3D build variations to their designs. ARAMIS Projected Net Shape Verification (PNSV) can measure the part shape with great precision relative to core reference points and the CAD design, in real-time. According to some embodiments, in-situ monitoring of the thermoplastic materials (such as, for example, the tapes) in accordance with the methods and system herein may be carried out in conjunction with an RVAT system (an augmented reality system for component assembly and archival baseline clone). The RVAT system is a system which records the as-built structure or component assembly, and represents the actual part built in CAD. An RVAT database may be generated or supplied that includes the CAD information for the substrate being constructed (e.g., such as a structure being built or a part). The RVAT database preferably includes the as-built information, including the CAD information for the actual substrate part being constructed, which may be termed a Digital-Twin (offering the capability to provide information pertaining to the actual location of the tape layers of the structure being built, so that when the structure is being built, not only is there the original CAD, but a CAD for the as-built structure). The application of the tape layup monitoring and quality of the build may be compared with the RVAT database, which may include the CAD for the structure, including where the tapes are to be positioned, as well as tolerances or limits for acceptable results for a build. The present system and method permit monitoring of the structure, and in particular the structure formed from the thermoplastic tapes, to detect changes as the structure is being constructed, even when the changes may not be visible to a human inspection. The in-situ monitoring may be documented (for example, as shown in FIGS. 3 and 4), and the measurements stored within the RVAT Database (the Digital-Twin) or other database to provide information about the structure being built. The present system and method may be implemented with RVAT Analytics to identify slight variations in response, exposing structural defects, all as the structure is being constructed.

Figure 6:
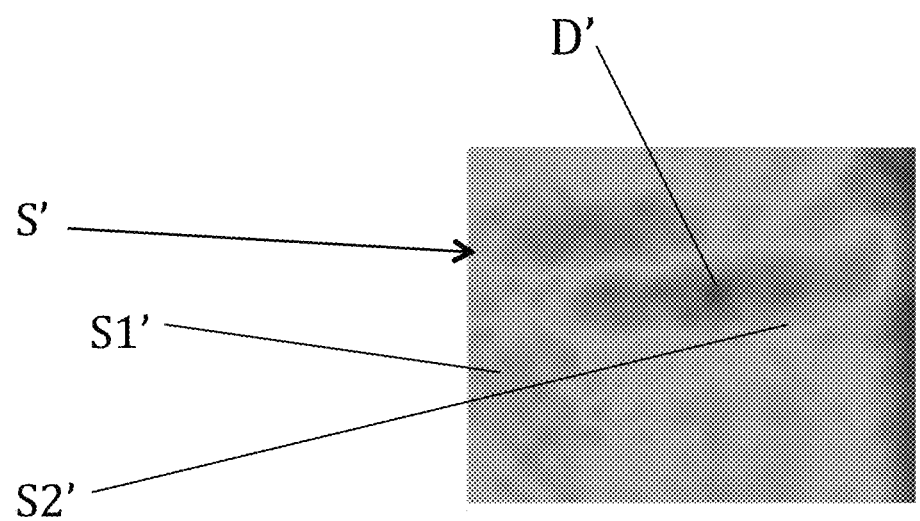
FIG. 6 is an image representing eddy current mapping to detect defects.

According to some alternate embodiments, an eddy current sensor may be utilized to provide feedback of the structure as it is being constructed, and in particular to monitor and evaluate the quality of the build where the thermoformable materials (e.g., thermoplastic composite tapes, or thermoset materials) are used to construct a structure. The eddy current may be measured using a high-frequency eddy current sensor that is provided on the head of the tape laying robot or on a separate sensing head that follows the thermoformable material as it is installed in position to form the structure (e.g., such as a tape laying head, robotic or manual). An example of the eddy current mapping of the detection results is depicted in the image of FIG. 6. As is shown in FIG. 6, the surface S' includes an area S1' of a first imaging depiction (in green), and a second imaging depiction S2' which identifies a defect D'. The eddy current monitoring and detection for defects may be used in conjunction with thermoformable materials. Some examples of uses for the eddy current sensing implementation include carbon epoxy and fiberglass layups. The eddy current detection may be utilized to determine the presence of near surface defects, and may be carried out in real-time as a structure is being constructed (or repaired).

Figure 7:
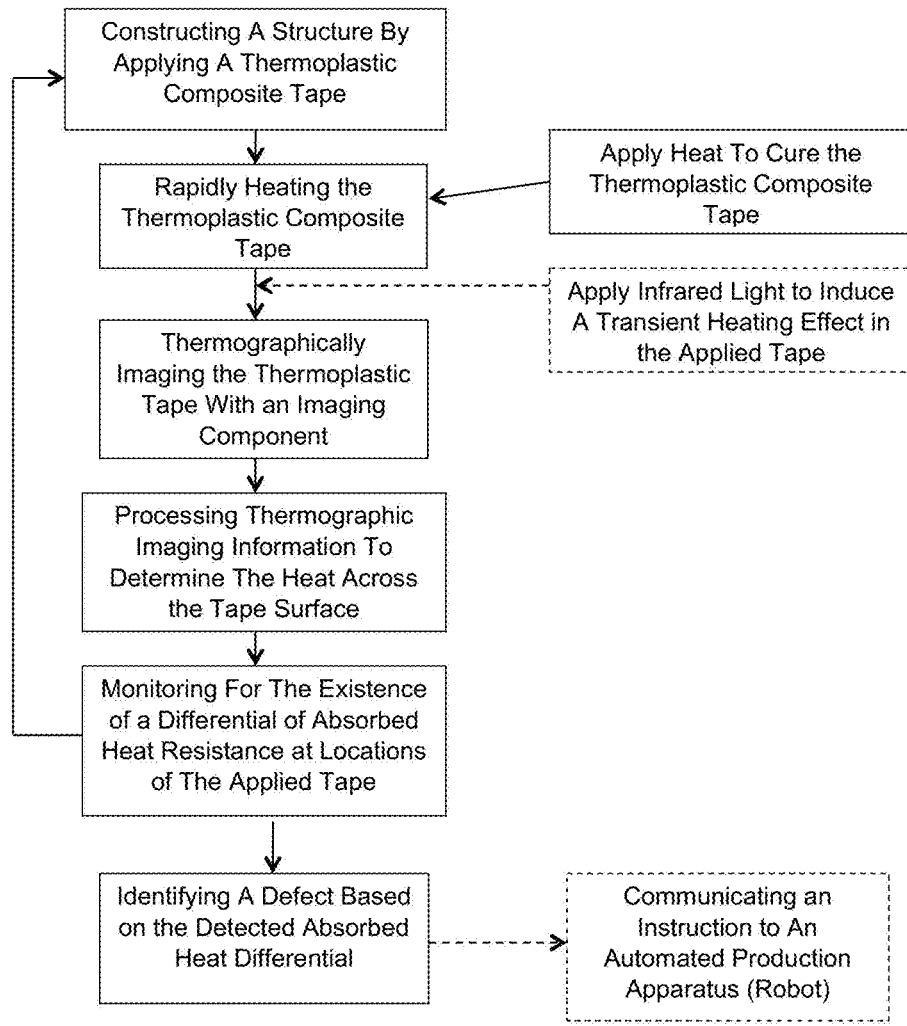
FIG. 7 is a flow diagram depicting an exemplary embodiment of the method for monitoring a composite structure being constructed for potential defects.

Referring to FIG. 7, a schematic illustration of a flow diagram is shown representing an exemplary implementation of the method for conducting in-situ monitoring of thermoformable composites. The themoformable composite is illustrated comprising a thermoplastic composite tape. The tape is applied to form a structure, and the application of the tape involves rapid heating of the tape to cure or set the thermoplastic in place to form the structure or portion thereof. The application of the tape is monitored by thermographically imaging the thermoplastic composite tape with an imaging component, such as an ARAMIS imaging system as described herein. In applications where the thermal heating to cure the thermoplastic composite tape is not of a suitable duration to determine the heat absorption or differential thereof, optionally, a thermal pulse or other applied heating, such as via infrared radiation, is directed to the tape to induce a transient heating effect in the applied tape. According to some alternate embodiments, applied cooling (e.g., TcNDE) is implemented to cool the surface, and a thermographic measurement of a differential is obtained by monitoring the cooled structure or surface as it warms. The thermographic imaging information is processed to determine the heat across the tape surface. The monitoring of the construction, and in particular, the applied tape, is carried out to determine the existence of a differential of absorbed heat resistance at locations of the applied tape. When a resistance is detected (and meets a threshold or level of potential concern), a defect is identified. According to preferred embodiments, the defect is signified by detecting an absorbed heat differential, and the location at which the differential is detected. The detection of a defect may optionally, according to some embodiments, trigger a communication with a robot or other automated production machine to react to the defect. The reaction may be to cease production, adjust a production parameter or positioning of the installation or construction, or undertake some other course of action. An alert also may be communicated to a human operator when a defect or other condition is detected from the heat differential. According to some implementations, both an alert (e.g., communication to a human) and a triggered communication to a robot may be generated.

According to alternate embodiments of the invention, in situ monitoring of composites may be carried out by Thermography Cool NDE (TcNDE), according to preferred methods and devices for monitoring the quality of a build. The TcNDE is different than traditional Thermography NDT. Thermography NDT (which has been discussed herein) uses radiant thermal heating, such as for example, with a halogen or xenon lamp, which heats an area of interest while the thermography statically watches the area cool. The Thermography Cool NDE according to embodiments, uses convective cooling to thermally stress the part, thereby drawing out the ambient heat.

According to a preferred implementation, the method involves cooling the surface of a substrate, such as the structure being constructed whose build or application of material (such as a composite tape or fiber application). A suitable cooling apparatus may be used and directed at the area of interest (e.g., area to be inspected or monitored). The area of interest (of the substrate) is monitored or scanned with a thermal imaging device, such as a thermal imaging camera. The imaging preferably images the cooling path warming (that is the substrate build area), so that the applied cooling is applied, and the warming of the area is imaged to record the thermal condition, and changes. Preferably, the monitoring is coordinated with the location on the structure, which may be done, as discussed herein in connection with other embodiments, so that the CAD image coordinates may be used to identify the location or locations corresponding to the imaging area, and enable pinpointing the location of any defect. The thermal differential identified from the warming of the structural area from its cooler state (at the monitoring location, which preferably is a location where a tape, or other thermoformable material, e.g., fiber material, or panel or sheet, has been placed manually or by a robot), and indications of defects or abnormal structural conditions are observed from the thermography. The thermography information may be processed and compared to identify any areas where the heating and/or cooling changes (e.g., differentials) come within or exceed a threshold that may indicate an abnormal condition or defect. While the thermography NDE used with an application of heat may also determine indications, as discussed herein, in connection with embodiments, the measurement of warming after an application of cooling is measured as a function of the heat leaving, and may have a single directional path, whereas a measurement after an application of heat may be subject to the incoming heat being applied to the surface and its reflection back as well as the material characteristics and physical properties.

According to a preferred embodiment, the imaging method for Thermography Cool NDE is carried out while a structure is being constructed, similar to the structures and constructions discussed herein in connection with the thermal heating or monitoring of a thermoformable material (such as a composite or material) after the application of heat (e.g., through the construction process to cure the material, or through added heat, such as a pulse or continuous beam). The cooling apparatus may be carried out with cooling directed at the location of interest, which in the build process may be the substrate, and may be used to monitor the application of a composite (e.g., tape or fiber) to a structure or surface.

According to some preferred embodiments and implementations, directed air is applied to the material in order to monitor the quality through thermography. A jet of cool air may be directed at the surface to be monitored. Brushing the surface with a jet of cool air is one way to effect cooling of the surface. Using the cool air method to cool the substrate (or item applied to the structure) is independent of material emissivity, as the substrate or surface being monitored is being convectively cooled.

Figure 8:
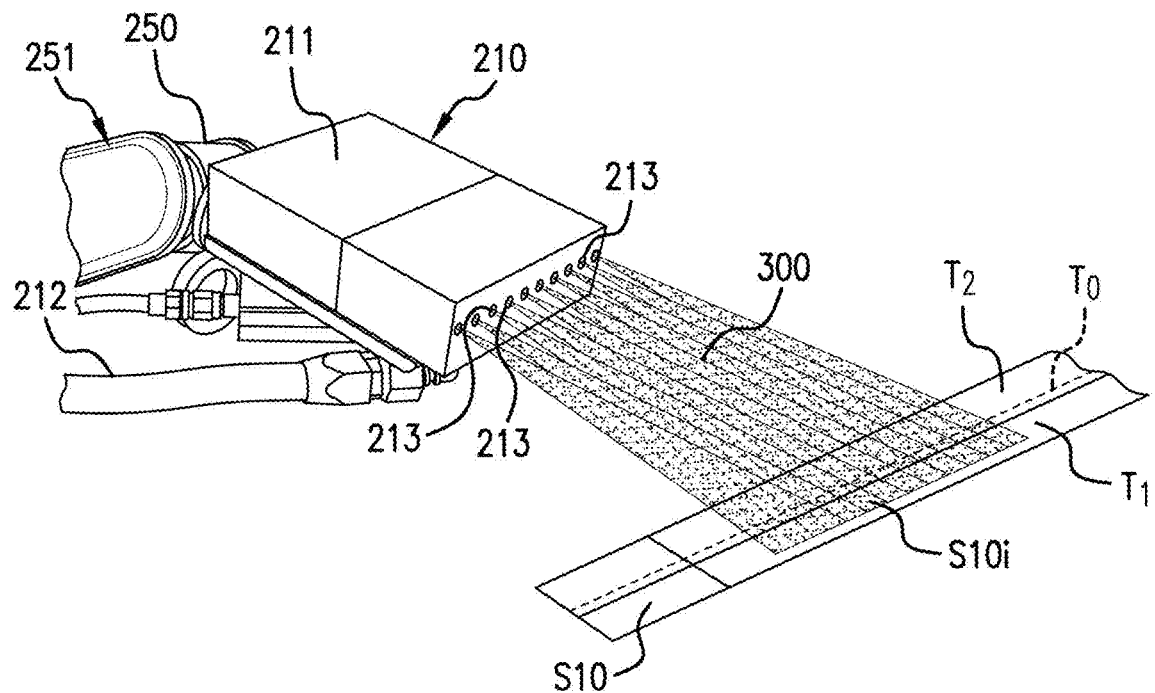
FIG. 8 is a perspective view of a device for delivering cooling to a structure or area of interest thereof, as viewed from the right side.

According to a preferred embodiment, a source of cooled air is directed to the substrate. The cooled air may be delivered from any suitable delivery device. An exemplary device includes a source of cooled air directed to a manifold, from which the cool air is directed to the surface being monitored, or one or more locations on the surface. The cooled air manifold may serve a single or multiple locations where the structure is being constructed and where monitoring of the build, such as the application of a thermoplastic or thermoset material, is carried out. An exemplary embodiment of a device for implementing the method of monitoring TcNDE is shown in FIG. 8. To facilitate directing air at a surface S10 and the location of interest S10$i$, a head 210 shown with a manifold 211 connected to a conduit or line 212 that supplies a cool gas source. The cool gas source may be air, or may comprise another suitable gas, such as, for example, an inert or non-reactive gas, like cooled CO2 or cooled N2. The source may be cooled with a cooling apparatus such as a compressor and coil, or may be delivered from a source that is ambient (so that relative to the area of the structure, the cool air source cools the surface). In the embodiment illustrated, the manifold 211 has a plurality of openings 213. The openings 213 may comprise apertures, delivery tubes, nozzles or other conduits situated on the manifold 211 so that a stream of cooled gas is delivered from the manifold openings 213. The gas or air preferably is pressurized so that it is jetted out from the manifold 211 at a suitable velocity to impart cooling of the surface S10 (so that the cool air continually replaces the air that contacts the surface and has taken on some of the heat from the surface to effect convective cooling). A cool air stream is shown in FIG. 8 represented by the reference numeral 300. Preferably, the manifold is situated relative to the object being monitored, and more preferably to the surface or area of interest (e.g., where the thermoformable build is taking place), so that the cool air stream 300 from the jet or manifold openings 213 brushes the surface S10. The Thermography Cool NDE scan (TcNDE scan) may be carried out using a robot with a thermal camera imaging the cooled path warming, which may be implemented as an independent scan of hand layup, or as part of the AFP robot head, testing the material as the material is being applied. In the embodiment depicted in FIG. 8, the manifold 211 is shown attached to the head 210, which is supported on an arm 250 forming part of the robot 251. The robot head 210 may optionally include one or more mechanisms for constructing the structure, such as a tape dispenser, heating end, or other element. A robot head may be configured similar to the robot heads shown and described herein in connection with the embodiments shown in the other figures, but with the cooling mechanism, such as the manifold 211, carried thereon for directing the cooling at the location of the structure where the thermoformable material is being applied (or has just been applied).

Figure 9:
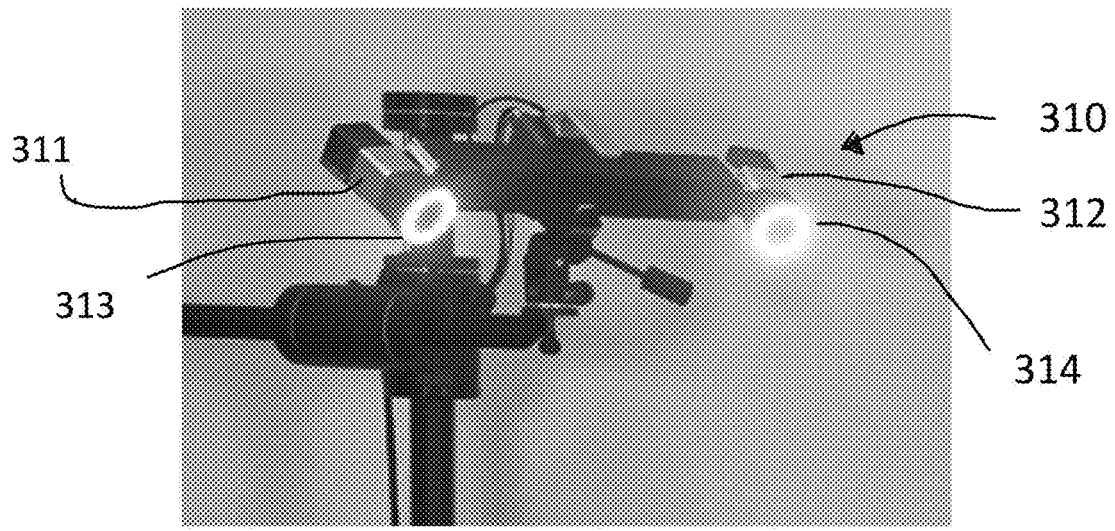
FIG. 9 is a front perspective view of an exemplary embodiment of an imaging component shown having a pair of cameras and a light source.

An imaging component, such as the system 310 shown in FIG. 9, comprising a pair of cameras 311, 312, each with an illumination source 313, 314, is directed at the structure and captures the build. The imaging component images the field and preferably tracks the robot head (including the cooling head, see e.g., 210 in FIG. 8, and any constructing elements thereon), and is used to determine, by processing of the inputs, the location of the structure and the corresponding thermographic scan information at the locations on the structure. The imaging component or system 310 also may be used to track the components and structure shown in FIG. 10. The system may identify the location of any defect determined from the Thermography cooling NDE (TcNDE). The system 310 may be configured so that it is directed at the area of interest, such as for example, that location S10$i$, and preferably captures the structure as the components are formed or installed thereon or to form the structure S10. In the example illustrated, a row of thermoplastic tapes is depicted and cooling is shown directed at the tapes T1 and T2. The tape may be installed in an overlapping fashion so that there is a slight overlap (To). The unit 210 (FIG. 8) preferably is carried on or may follow a separate robot or robot head that is used to implement the thermal joining of the composites, such as the tapes T1 and T2, to form the structure S10. According to some alternate embodiments, the components of the imaging system 310, such as, for example, the cameras 311, 312, and illumination sources 313, 314, are arranged proximal to a robot and/or the thermographic camera and equipment (heating or cooling apparatus) so that the imaging takes place directed to a particular location, the location where the components (e.g., T1 and T2) are being joined or installed.

According to some embodiments, the robot may be configured to carry out one or more steps of an assembly operation, such as for example, to construct a structure using a thermoformable material, including for example, as discussed herein. The cooling mechanism may be provided as part of the robot, such as, for example, where the robot is configured with a manifold 211 and/or one or more delivery nozzles or openings 213 for delivering a jet of cool air to the surface being monitored (such as a surface of the structure that is being constructed with a thermoformable material (e.g., tape or fiber)). The robot may carry a manifold 211 through which cooled air (or other gas) is directed. The manifold air stream preferably is directed at the area of interest being monitored which is the location of the thermoformable material application. The robot head 210 may be movably provided, and may operate in 6 degrees of freedom, so that the cooling air is directed at the site of the structure where the material is being applied, as the material is continued to be applied. The robot head 210 preferably follows the applied material (thermoformable tape or fiber), as the material is being applied to the structure. In some instances, where the robot head is itself applying a thermoformable material and/or carrying the heating source for the curing of the material, the cooling air manifold may be disposed on the robot to be positioned to follow the build, and deliver air to the area of interest (the site of the thermoformable material application), as the structure is being built. According to other embodiments, the cooling air is delivered by a robot head that follows the build and carries the cooling mechanism thereon (e.g., manifold 211), such as in the case where the material is being applied by hand and the robot follows the build, or in the case where a separate robot head is operating to lay up the material and/or cure the material.

The manifold preferably serves the one or more nozzles, which may be connected through a suitable line or conduit that connects the manifold to the delivery nozzle or nozzles. According to some embodiments, the manifold may have nozzles provided thereon which may be directed at the area of interest to be monitored.

Figure 10:
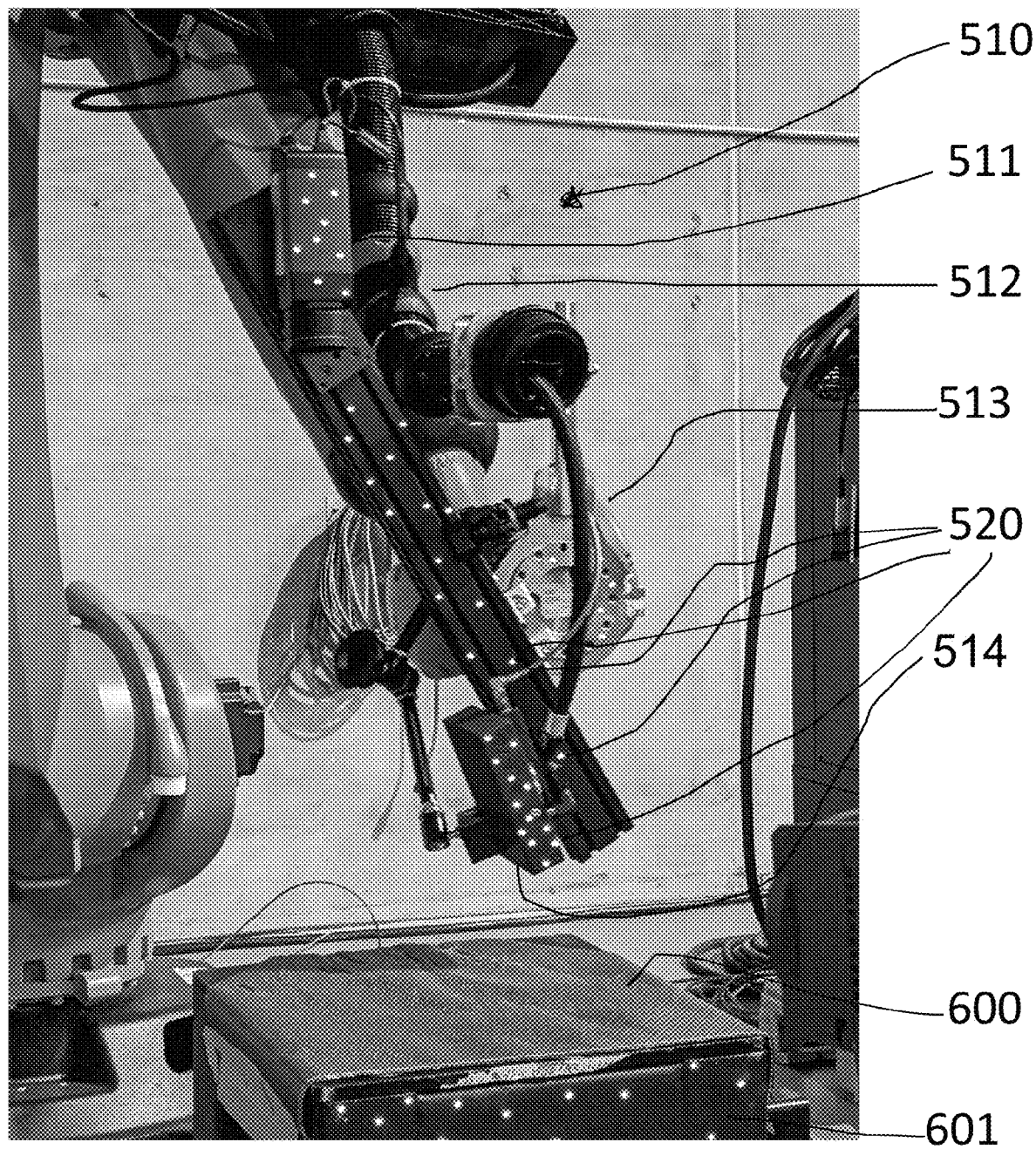
FIG. 10 is an exemplary perspective view of a robotic device constructing a structure, shown with a thermal imaging camera carried on the robot, and with a field imaging camera imaging the location where the structure is being constructed.

Referring to FIG. 10, an exemplary embodiment of a system 510 is depicted where a thermal imaging camera 511 is mounted on a robotic arm 512 of a robot 513. A cooling head 514 for delivering a cool stream of air or other gas is also shown, and according to a preferred embodiment, is directed ahead of where the thermal camera 511 looks, providing a short time interval for the cooling to be applied prior to the thermal imaging to observe the return of the structure to an elevated temperature (i.e., warming after the cooling is applied). One or more and preferably each of the robot 513, robotic arm 512, thermal camera 511 and cooling head 514 have tracking indicia thereon, which in this illustration comprises a plurality of photogrammetry dots, generally referenced as 520. The composite material 600 is shown depicted on a frame or support 601 (which according to some embodiments may comprise an existing structure to which the material is being applied). The support 601 in this exemplary depiction shows a plurality of photogrammetry dots 520 provided thereon. The cooling head 514 may be similar to the manifold shown and described above in FIG. 8. The robotic arm 512 is tracked with a field imaging device, preferably a camera, such as the camera shown and described herein, such as an Aramis stereo imaging camera, e.g., for example, the camera shown in FIG. 9.

In the depiction illustrated in FIG. 10, the structure is constructed by placement of composite material 600 onto the structure to be constructed, and using the robot 513 to apply the cooling stream of air or other gas from the cooling head. The camera 511 preferably comprises a thermographic imaging component, such as a thermal (IR) camera. The photogrammetry dots on the camera 511, robot 513 and cooling head 514, and the support 601 are used to determine the position where the imaging is detecting the quality on the material or structure 600. According to some embodiments, a file containing CAD coordinates of the structure being constructed is provided and the imaging it tracked relative to the CAD of the structure. The CAD may be generated by any suitable means, including an actual mesh of the structure or a component thereof. The dynamic photogrammetry also facilitates following the component and assessing the quality as the component or portions thereof are put into position or make contact with the structure or other component to which it to apply. The field imaging camera (which in this example is located behind the robot and out of view) is positioned and calibrated to track the thermal (IR) camera, and infer the precise location of detected defects in the structure coordinates, such as CAD coordinates.

The method, system and apparatus for the TcNDE preferably involves imaging the head that is involved in the production or construction of the structure, as well as the head that provides the cooling. According to some embodiments, the a robot or head may be configured with the cooling and the imaging components, while in other embodiments, the imaging components may be separately provided. In each case, the present dynamic photogrammetry system (such as for example, commercially available systems ARAMIS/PONTOS/ATOS from Gom GmbH) can image the precise location of the TcNDE head, to precisely know where the defects are located during the dynamic scan. This is done with the 3D dynamic photogrammetry imaging the 6-DOF (6 degrees of freedom: X, Y, Z, Roll, Pitch, Yaw) of the robot head, so the calibrated system knows precisely where the TcNDE system is looking on the surface defined by the CAD coordinates of the structure, which the dynamic photogrammetry system measures. The TcNDE system, similar to the other embodiments discussed herein, preferably comprises a thermal camera that is provided to image the thermoformable materials being applied to the structure (i.e., to form the structure). The photogrammetry system images the TcNDE head as well as the structure being constructed, and therefore, identifies the location of the imaging so that any imaging information, including identification of a defect or condition, may be pinpointed to its location on the structure. Preferably, the locating feature is carried out in association with the CAD for the structure. The locating preferably processes the information from the CAD, which may comprise x,y,z coordinate information, as well as the thermographic information obtained from the applied cooling and resultant effect exhibited by the material (e.g., the thermoformable material being applied).

The system may be utilized to monitor and identify defects or conditions in a structure being constructed, where the structure or construction preferably is carried out by applying a thermoformable material, and heating to cure the thermoformable material in place. As discussed herein, thermoformable material may include and is not limited to, thermoset and thermoplastics, including thermoplastic composite materials, thermoset materials, thermoplastic composite tapes, fiber tapes, fiber or tape sections or panels, metallic composites and the like.

According to some preferred embodiments, the imaging of the thermal properties ascertained for a thermoformable material, such as a thermoplastic, thermoset, or metallic composite, may be obtained in real-time as the construction or build process is being carried out. The thermal imaging information obtained is coordinated to the location where the composite material has been placed. According to some implementations, the devices and methods determine quality of the build or structure by the application of heat or cooling.

The rate of temperature changing at a location and the final differential temperature is utilized to produce information which is represented as a color on a thermograph. The colors represent values and what may be relative normal values for the structure or component (or portion thereof), and values that are indicative of an abnormal rate of temperature change (after the applied heating or cooling has been introduced to the structure or component). A constant denoting a normal rate of change for the thermal condition imparted on the structure (such as heat or cooling) is determined, or has previously been determined (such as from a completed known acceptable structure or component). The constant is applied to the thermography information determined with the thermal imaging apparatus. The rate is therefore determined to indicate rapid cooling or heating when the temperature affecting step (cool air or heat) is applied, and the expected temperature elevation (from the cooled state) or temperature decline (from the heated state) is measured across the areas of the structure. According to some embodiments, the quality determination preferably takes place during the build, and the thermal camera is moved across the structure, and according to other embodiments, the quality determination is carried out after the structure is built (and in some cases both during and after build).

According to preferred embodiments, the information is transformed into a further voxelized representation of the structure, with each voxel representing a voxel value relative to the potential thermal imaging representation. The voxel values and their representation may be scaled to provide relative information for a location of the composite material that has been applied. A constant or a scaling value may be used to further differentiate the presence of a defect and to make it more readily pronounced. For example, where a variation in the respective heating or cooling is observed as part of the quality testing (depending on whether the material is heated and cooling is observed or whether the material is cooled and heating is observed), the voxelization may generate variations that depict the corresponding areas of the structure or the component applied. The locations of the defect as well as the extent and size of the defect are identified. Among some of the defects that may be observed include, for example, where a void, or bridging is present, or where a foreign object is present within a layer or layers of material. The voxelization may be done on a voxel size of 1 mm×1 mm cube, or may be adjusted based on the tolerances, such as for example, to a 1 inch×1 inch cube. The imaging information is obtained by applying the heating or cooling to the structure or portion, as described and/or shown herein using the applied heating (or heat from the build procedure), or applied cooling, and measuring the thermal differential after the heat or cooling has been applied. The measurement is performed at the locations of the structure, preferably where the component such as composite material has been applied, and the locations are identified using imaging equipment that is arranged to capture the structure as the build is being carried out.

According to preferred embodiments, the thermal imaging of the structure or component is aligned with the structure CAD or actual mesh. A stereo camera is employed to image and capture the structure and component being applied. A preferred application is the use of photogrammetry tracking of the thermal camera and the structure. As discussed herein and in conjunction with my prior pending applications, the imaging may be carried out by providing the field imaging component separate from the thermal imaging camera, which may include in its field of view the structure. According to some preferred embodiments, where composite material is being robotically applied, the field imaging component preferably images the thermal imaging camera and/or robot as well as the structure and composites being applied. Preferably photogrammetry markings, such as dots, are provided on the robot and the thermal imaging camera carried on the robot. The location of the thermal imaging camera and the location that it is imaging (the structure) are therefore identified. The thermal imaging information therefore is obtained in conjunction with the location on the structure or portion thereof to which the imaging information corresponds.

Figure 11:
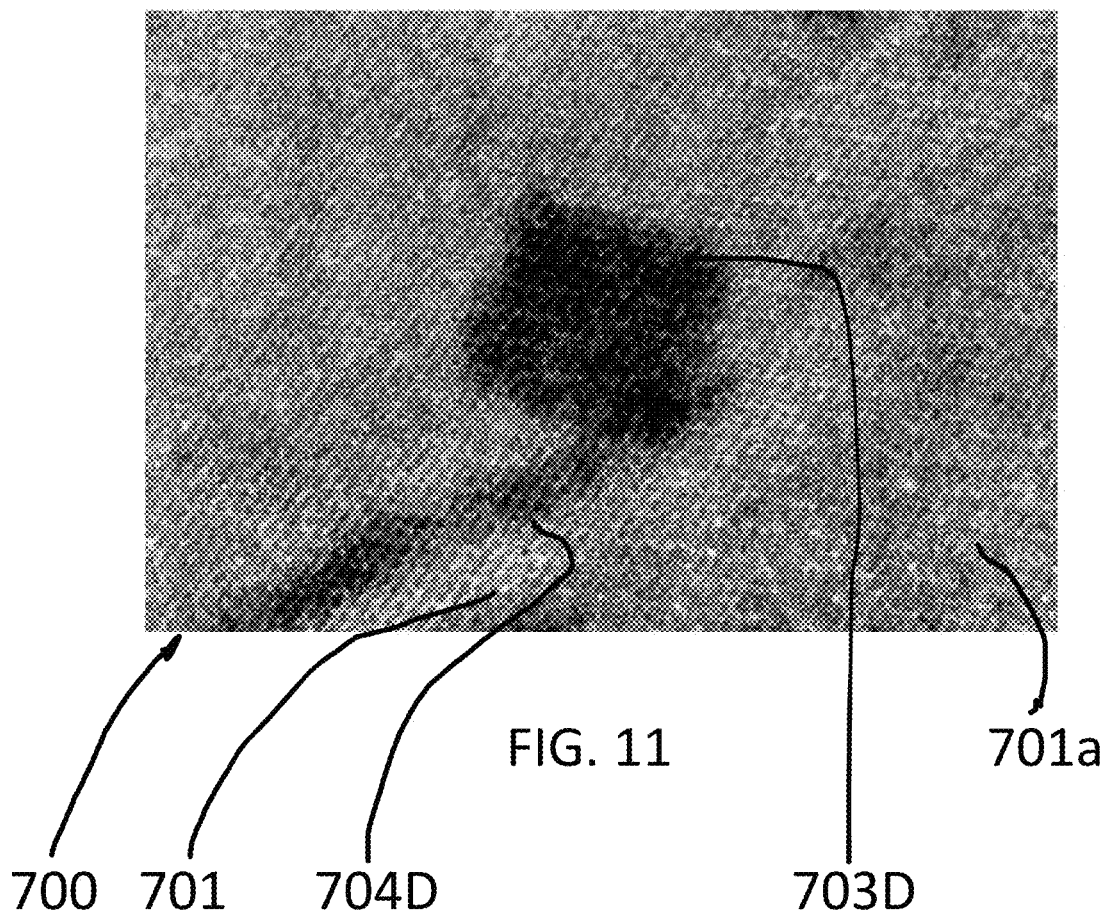
FIG. 11 is a thermography image representing a structure that contains a defect.

Referring to FIG. 11, a thermography image 700 is depicted representing a structure 701 that contains a defect (as indicated by the darker contrasting areas). The structure 701 for example, may be the structure 600 being formed in the exemplary depiction of FIG. 10. According to some embodiments the thermographic image, such as the image shown 700, may indicate a defect, such as a piece of a glove, a fuzz or thread from material being applied, or other artifact that made its way onto a panel thermoformable material being used. In other instances, the quality may detect not a foreign object, but a defect in the object being applied, or in the application or result of how it is being or has been applied. In the depiction of FIG. 11, the image 700 is provided to represent a thermoformable composite, such as a thermoplastic, thermoset or metallic composite being applied. The image 700 shows the surface 701a of a structure 701. The structure 701 may be a composite material that is applied to form the structure. In the depiction illustrated, the quality of the construction is determined as shown and described herein, and the quality is monitored and evaluated in real time, as the structure is being constructed. The defect 703D shows a first defect in the bonding, while a second defect 704D is also shown, (spanning diagonally) also representing a defect in the bond quality. The first defect 703D indicates that the application of the composite was not proper in the location (e.g., due to a foreign body), while the second defect 704D identifies a condition known as bridging, where the material has raised slightly instead of making a proper bond. As indicated, the relative warming of the structure 701, and the surface thereof 701a, demonstrated a differential, where the defects 703D, 704D are present. The system may also identify the types of defects and provide a quality indication, so that where a first type of defect is identified during the construction that may be remediated by continued layering, rolling and/or pressure applications during the build, the defect location may be continuously monitored, or depending on the structure may be deemed an acceptable tolerance threshold. Conversely, another type of defect, such as a second defect, for example, where bridging is identified, and/or a defect that would not be remedied by continued process steps in the build (or the tolerance is high), when detected, may be used to prevent further construction operations on that structure (partially constructed structure). The image while shown as a thermograph, preferably, according to some embodiments, may be represented instead through calculations which may apply a scaling constant to represent the thermal flux or heating/cooling differential detected in the composite structure formation, the thermal information is also coordinated with the imaging, such as a the photogrammetry to not only provide differentials that may identify the presence of a defect, but also that may indicate the location of the defect, and through location may also provide the type of defect (twist in tape, foreign particle presence, disbonds or bridging, and the like).

The method for in situ monitoring may be carried out using cooling to thermally stress the object of interest and using a thermal (IR) camera to image the rate of warming of the structure back to ambient. According to embodiments, a reduced rate of warming (i.e., back to ambient, from the cooling) typically is an indication of defective structure in that area, such as an air void, backing material or part of a glove, etc. The reduced rate of warming may be determined relative to the rate of warming of the surrounding structure or material that is being monitored (e.g., the portion of the structure or material surrounding the location where the reduced rate of warming has been detected). During the construction or build of a structure, the thermoformable materials may cure with the defect. The present TcNDE system enables defects and conditions to be identified during the construction process, so that materials, time and costs may be conserved. According to preferred embodiments, the cooling is carried out using convective cooling to thermally stress the material. Preferred embodiments utilize gasses such as cool air, cold CO2, and/or cold N2 (though other cold inert gases may be used). According to some embodiments, ambient temperature gas or air may be sufficient to impart the desired cooling required, while according to preferred embodiments, the gas or air is cooled so that it is cooler than the ambient temperature. The application of the cooling air (or other gas) may be carried out using a brushing method to cool the surface of the specimen while imaging the radiant change of heat with a static thermal (IR) camera imaging all or part of the structure. The IR camera is positioned to record the structure or part of the structure. According to another embodiment, the method may also utilize applied heating, which may be done after the cooling of the structure. For example, the cooling of the surface of the specimen is carried out, preferably using the brushing method while imaging radiant change of heat with a following thermal (IR) camera imaging the part of the structure that has just been cooled, thereafter the just cooled structural area is warmed up across the FOV (field-of-view), and the imaging is carried out to determine the differential across the surface relative to the warming. The image is processed to identify defects or conditions, such as voids, delaminations, backing material, and/or foreign objects, such as, for example a piece of a glove.

The method and system may be carried out for manual construction applications, as well as automated or robotic constructions. For example, scanning a just hand laid-up composite ply may require multiple passes to test the entire ply layer. The scanning may be carried out using a robotic head that is directed to scan the substrate surface or area of interest. The scanning also may be carried out by hand, by passing a scanner over the area of interest (e.g., the area where the thermoformable material has been applied).

The system may be employed on an AFP/ATL Head in order to check the quality of the just laid material, such as the just laid composite tape. According to some implementations, the cooling mechanism, such as the manifold 211, may be provided on the AFP/ATL head, or associated with the head, so as to follow the head and direct cooling at the just laid material (e.g., the composite tape). For example, the delivery of cooled gas from the cooling mechanism manifold may be directed to the area of construction. The head may be configured to lay the tape, heat the tape as needed, and then follow with directed cooling to that location, and the tape lay-up continued. The configuration, according to some preferred embodiments, provides for the tape lay-up to lead, followed by or in association with the heating to cure the thermoformable tape, and then followed by cooling. The thermography is carried out by imaging the tape lay-up and cooling to identify defects or conditions of the structure as it is being constructed. According to preferred embodiments, dynamic photogrammetry is employed calibrated to the track the thermal (IR) camera and infer the precise location of detected defects in the part coordinates, such as CAD coordinates. The thermal IR camera field of view is determined by the dynamic photogrammetry tracking. According to preferred embodiments, the dynamic photogrammetry tracking of the thermal IR camera is carried out as the IR camera moves to follow the construction, such as the tape being laid up.

The methods, systems and devices may be utilized in conjunction with thermoformable materials, including the thermoformable materials described herein, such as thermoplastics and thermosets. In addition, the present method and devices may be implemented to monitor the assembly or construction of a structure that is constructed using a thermal welding process. Some examples of welding processes that may be monitored with the present systems and methods include frictional heating (such as spin welding, ultrasonic welding, or vibration welding), electromagnetic heating (e.g., induction, microwave, dielectric and resistance welding), bulk heating using for example, hot melt adhesives or dual resin bonding, and thermal techniques such as hot plate, hot gas or radiant welding, which may include infrared and laser applications to deliver heat. The thermal welding preferably uses fusion to join parts or materials together.

According to some embodiments a welding application may be used to join together one or more parts or materials to form an article. The welding may comprise joining one or more materials to form an article, or may join a material or materials to an existing component, frame or structure, in order to complete a step for or the formation of a structure. The welding preferably is implemented for thermoformable composites and more particularly for thermoplastic composites, which also may include reinforced thermoplastic composites. The thermoplastic composites that may be utilized in accordance with the embodiments described herein also include thermoplastic matrix composites, as well as other thermoplastic and thermoformable composites used to construct products, such as, for example, aircraft and aerospace structures, as well as in marine and industries. The thermoplastic welding implementations may utilize the thermoplastic as a hot melt adhesive. According to some embodiments, the thermoplastic materials may be welded together.

In accordance with a preferred method, the system is configured to monitor the quality of the thermoplastic weld or bond being formed by the construction of the structure. As discussed herein in connection with the NDE for thermal heating and thermal cooling implementations, the thermographic image is obtained for the welding bond, which preferably may be a thermoplastic material, or materials. The joining together of a material to another, or two materials together, at the weld area is monitored using the monitoring system described and depicted herein in connection with the other embodiments. The welding may be carried out using manual techniques, or more preferably by implementing one or more robots to position and deliver the material, and/or to apply heat to weld the thermoformable material, such as a thermoplastic material. The robot may carry the thermal imaging component or components, or according to some alternate embodiments, the thermal imaging components may be separately provided, which includes providing them on a separate robot.

According to preferred embodiments, the system and method may be provided and implemented as discussed herein in connection with the NDE monitoring embodiments and depicted in the various figures of this application. The system and method may be utilized to determine detection of defects in thermo-welding applications, such as construction of thermoformable structures and articles using a thermal bonding or fusion technique. The system and method detect defects, including, for example, foreign object debris and/or foreign object damage (FOD), as well as the quality of the bond and the alignment of the structures being formed or components being thermally joined together. This may occur in robotic assemblies where thermowelding is being carried out with the use of a robot that carries a welding source (such as a heating, ultrasonic, electronic or the like) to deliver the energy to melt the thermoplastic material, as well as where the same robot or one or more other robots are employed to deliver the thermoplastic material or adhesive to the bond location (such as the joining location).

As with the other embodiments shown and described herein, in-situ thermographic measurements may be carried out using an infrared camera (IR camera) as the imaging component to image the cool down of the weld, and preferably once the weld has been formed. This can be accomplished by imaging the weld area with the IR camera so that the capture of thermal information of the weld is obtained as the weld is being formed, which also may include prior to formation, during the formation of the weld, and after the weld is cooling or curing (i.e., when the thermal energy source is no longer being applied to that weld location). The imaging collects and processes the thermographic information from the materials at the joining location of the weld as the area or weld cools from the elevated welding temperatures (e.g., 750 degrees F.) to near ambient during a build. During a pass with the robot or imaging robot, the joining area where the weld takes place will cool down across the sensor image, providing measurement of the thermal flow across the weld area and the materials being joined together. The processing of the image information may be carried out with a computer having a hardware processor and software stored on a storage component or media (e.g., hard drive, flash drive/memory, or chip), that contains instructions for capturing the thermal image information and processing the information to determine whether a defect is present, and preferably where the defect has been identified. The CAD file and coordinates preferably are utilized for the structure being constructed and/or components being installed, as discussed herein in connection with other embodiments. The CAD information coupled together with the imaging information provided by the real time thermal scan (or subsequent storage and analysis), enable the location of the build and any defect or observable condition to be identified on the scan, and the thermal imaging scan being observable at the specific location on the component.

This imaging provides a good measure of the weld quality at the weld location, and a thermal image across the weld during the process is obtained. However, at any one time, the imaging information may be processed, and the weld quality examined to determine whether a defect is present or indicated, or another condition of interest is warranted. The system, as with the other embodiments shown and described herein, therefore may discontinue the weld process so that a defect may be addressed. According to some configurations, the system may include an instruction for the robot (or technician) to remove the defective weld (or components), and reform the weld, or replace the component and reinstall it. In the case of the thermoplastic materials, the repair procedure during a build may be carried out to reform the thermoplastic material and replace it. The method and system permit thermoplastic welding to be carried out, so that defects may be addressed as they become present or are created. This saves time and money, since the fabricators need not wait until the final part, structure or assembly is completed before determining whether there is a defect. The present in situ monitoring methods and systems reduce or eliminate the potential for structure failures. For example, some defects may not be able to be pinpointed or observed until after the structure is assembled. There are also instances where the defect may be among other layers or part of a component used to make another part or structure (or sub structure). In these cases, where a defect is permitted to otherwise be maintained in the part because it is not detected, the part could still pass, due to the defect being in a location that is not part of the final testing or escapes final testing, but is nonetheless a potential contributor to a potential failure of the ultimate structure, or the reduced service life or overall strength of the structure. The present invention facilitates detection of a defect prior to the defect being able to make its way into a completed or final product.

The system may process the thermal flow information and identify whether there are any abnormalities or areas of concern present. The system may conduct processing in the form of issuing and/or communicating an alert, stopping the automated process (AFP/ATL), or undertaking some other action (e.g., align the robot or automated machine). The processing of the image information may be carried out with a computer having a hardware processor and software stored on a storage component or media (e.g., hard drive, flash drive/memory, or chip), that contains instructions for capturing the thermal image information and processing the information to determine whether a defect is present, and preferably where the defect has been identified.

According to some preferred implementations, the method and devices improve the operation of the computer by integrating build steps with the imaging as the structure is being constructed. The thermal imaging information is related across the surface being monitored for quality, which according to some embodiments, directs robotic operations as the structure is being formed. The thermal imaging camera preferably provides the thermal information for the location that the field imaging camera pinpoints, preferably using photogrammetry with indicia such as photogrammetry dots located on the surface of the thermal camera and/or a robot, or other structure. The imaging information is correlated to provide relative correlations of the surface being imaged, preferably, where the construction (application of a thermoformable material, such a thermoplastic, thermoset or metallic composite) is taking place. The processing of the information may scale the information to identify relative heating or cooling differentials in response to applied heating or cooling. A defect or other condition therefore is identified by the relative differentials in the heat flux, and more particularly the rate of heat leaving, i.e., cooling, or the rate of warming, i.e., heating. The structure preferably is constructed in a real time operation that applies a thermoformable composite material (e.g., thermoplastic, thermoset or metallic composite materials), and determines the quality as the material is being applied. The quality also is determined to guide the next operations, such as with the robot operations, and or in some instances, a human operator.

The system and method may be used to track the structure during a build. As mentioned herein, the RVAT system used to record an as-built structure or component assembly, and represent the actual part built in CAD, may be implemented in conjunction with a photogrammetry system with projected DIC (Digital Image Correlation) that may be used for 3D shape measurement of the building part. The 3D shape measurement can be directly compared to the CAD of the part in real-time, to track build errors, during the build. The present in-situ monitoring system may be employed in conjunction with the RVAT system to monitor the quality of thermoformable builds, and generate a warning to an operator, or to use the thermographic monitoring information to repair the build, during the build, automatically (such as where a robot or other automated machine is used to carry out the build).

The present system and method may be utilized in conjunction with an in-situ strain measurement. According to preferred embodiments, an ARAMIS system (utilizing a camera or other image sensor, and light for imaging of the structure being built) may be used in conjunction with the present system and method to determine strain measurement. The present method and system preferably may determine strain measurements as the structure is being constructed. According to some implementations, the thermoplastic used to construct the structure preferably may have a pattern displayed on its surface. In some instances, the pattern may be such that it appears at all times during the build process, and according to other embodiments, the pattern may be provided to be visible at particular temperatures or temperature ranges (including at least one initial time where a baseline of the pattern may be obtained). According to some embodiments, the thermoplastic components that are used to construct the structure, such as the thermoplastic tapes, are patterned. The pattern preferably is a pattern that is useful for carrying out digital image correlation (DIC), such as a random pattern, or pattern of ellipse or ovals, or combinations of shapes, that enable the determination of strain based on the deformation of the material (and hence the pattern). The patterns and their application for strain determinations may be implemented as set forth in my co-pending U.S. patent application Ser. No. 16/236,081, filed on Dec. 28, 2018, for an invention in optical structural health monitoring. Patterned thermoplastics may be measured for 3D shape directly (without a need for projection), and also may be measured for strain (which is not possible with projection). During cool-down, the strain may be used to estimate material properties or detect manufacturing defects. The present system and method monitor the build and the cool down of the thermoplastic material, such as the tapes. The ARAMIS measurement of the final layer, after mostly cool, can be used as a baseline for manufacturing strain measurements, and for life long structural health monitoring. Long-term monitoring may be carried out utilizing the present system's capability to store and register future measurements with the reference image or data, such as using an RVAT database.

While the invention is described through the above-described exemplary embodiments, it will be understood by those of ordinary skill in the art that modifications to, and variations of, the illustrated embodiments may be made without departing from the inventive concepts disclosed herein. For example, although some aspects of the system and method have been described with reference to a flowchart, those skilled in the art should readily appreciate that functions, operations, decisions, etc. of all or a portion of each block, or a combination of blocks, of the flowchart may be combined, separated into separate operations or performed in other orders. According to some embodiments, thermographic imaging sensors may comprise infrared imaging sensors, eddy current sensors, or both. Moreover, while the embodiments are described in connection with various illustrative data structures, one skilled in the art will recognize that the system may be embodied using a variety of data structures. Furthermore, disclosed aspects, or portions of these aspects, may be combined in ways not listed above. Accordingly, the invention should not be viewed as being limited to the disclosed embodiments.

What is claimed is:

1. A method for determining the quality of a structure, wherein constructing the structure includes the use of a thermoformable material comprising a thermoplastic, thermoset or metallic composite, and applying heat to the thermoformable material, the method comprising:
   a) capturing with an imaging device information pertaining to the structure and at least a portion of a component comprising the thermoformable material being applied to construct the structure,
   b) wherein capturing with the imaging device is carried out as the component of the thermoformable material is being applied to construct the structure, or after the thermoformable material has been applied, or both during the application and after the application of the thermoformable material to construct the structure;
   c) wherein said imaging device comprises a thermographic imaging component;
   d) processing the captured information from step a), including determining a differential heat flux of the applied component cooling after the application of heat, or determining a differential of heat flux of the applied component heating after the application of cooling; and
   e) determining, as the structure is being constructed, from said processing whether the differential of the heat flux of the applied component cooling or heating indicates a defect;
   f) tracking the thermographic imaging component and its location relative to the to the structure and at least a portion of the component comprising the thermoformable material being applied to construct the structure;
   g) wherein tracking in step f) is carried out as the imaging component is moved to image the structure or portion of the component comprising the thermoformable material being applied to construct the structure.

2. The method of claim 1, wherein applying the component to construct the structure includes heating the component or allowing the component temperature to rise to thermally form the structure or portion thereof.

3. The method of claim 1, including applying heating or applying cooling to the location where the thermoformable component material is added to the structure, and wherein in step d, the application of heat includes the heating applied, and wherein in step d, the application of cooling includes the applied cooling, and wherein capturing with the imaging device in step b) is carried out as the component of the thermoformable material is being applied to construct the structure.

4. The method of claim 3, wherein the application of cooling comprises applying cooling to the structure via a stream of a cooling gas.

5. The method of claim 3, wherein application of heating comprises application of an infrared heating source.

6. The method of claim 1, wherein said thermoformable material comprises a robotically applied tape, and the method includes robotically applying the tape.

7. The method of claim 1, wherein the differential heat flux of the applied component cooling or applied component heating is determined with the Thermography In-situ Inspection (TII) or Thermography NDI (Non-Destructive Inspection).

8. The method of claim 7, including determining a location of the component being applied to construct the structure, wherein the location comprises the actual location of the component being applied relative to the CAD coordinates for the structure.

9. The method of claim 8, wherein the component actual location is the imaged location, and wherein said component location relative to the structure comprises the component actual location and the structure actual location as determined by the structure's reference to the CAD coordinates of the structure as determined by the imaging of the structure and relating of the structure to the CAD coordinates for the structure being built.

10. The method of claim 1, wherein determining whether a defect is present, when heating is applied in step d, is determined based on the differential of the absorbed heat resistance at the location of the defect compared with one or more locations where the defect is not present; and wherein determining whether a defect is present, when cooling is applied in step d, is determined based on the differential of the rate of warming at the location of the defect compared with one or more locations where the defect is not present.

11. The method of claim 1, wherein determining the presence or absence of a condition in the structure being constructed is based on the heat differential of the cooling of the component being applied when heating is applied in step d, and is based on the heating of the component being applied when cooling is applied in step d.

12. The method of claim 1, wherein the detection of a defect is determined based on the detection of an absorbed heat resistance at the location of the defect when heating is applied in step d, and wherein the detection of a defect is determined based on the detection of a reduced rate of warming of at the surrounding structure at the location of the defect.

13. The method of claim 1, wherein the structure is constructed using one or more robots, wherein said thermoformable material component is robotically applied by operating said one or more robots to form the structure, and wherein when a defect is detected by the indication in step e), stopping the robot to cease further robotic construction of the structure.

14. The method of claim 13, wherein when a defect is detected by the indication in step e), operating the one or more robots to remediate or address the defect condition.

15. The method of claim 13, wherein said one or more robots comprises at least one tape laying robot, and wherein said defect condition is the between adjacent courses of tapes being laid with the robot, and wherein operating the one or more robots to remediate or address the defect condition comprises adjusting the position of the robot to the correct gapping or lapping position.

16. The method of claim 15, including controlling the at least one tape laying robot with a computer, and wherein said computer includes software containing a program with instructions to operate the at least one tape laying robot to apply the tape to the proper location, said software including instructions for processing the image information and controlling the operations of the at least one tape laying robot to construct the structure by applying the tapes to avert the formation of defects in the final structure.

17. The method of claim 15, including controlling the at least one tape laying robot with a computer, and wherein said computer includes software containing a program with instructions to operate the at least one tape laying robot to apply the tape to the proper location, said software including instructions for processing the image information and controlling the operations of the at least one tape laying robot to construct the structure by applying the tapes to avert the formation of defects in the final structure, wherein said adjacent courses of tape include a first course of tape, a second course of tape, and a third course of tape, wherein said second course of tape is laid at least partially overlapping said first course tape, and wherein said third course of tape is laid at least partially overlapping said second course of tape, wherein said second tape includes an area where there is no overlap of an adjacent tape, said area defining a gap, and wherein the method includes monitoring the gap to determine the quality of the structure being constructed.

18. The method of claim 17, including communicating an instruction to said robot to adjust the positioning of the applied tape to correspond with the designated position of the tape to produce the appropriate gap or lap, or improve the build to overcome a previously detected defect.

19. The method of claim 1, wherein determining whether a defect is present includes determining the bond quality of the thermoplastic material component, and wherein determining the bond quality includes determining whether one or more of a void, foreign object, twist, improper lap or improper gap, or bridging is present in the applied component or structure.

20. The method of claim 1, wherein applying heat to the thermoformable material component thermoforms the component on the structure, and wherein after heating to thermoform the component on the structure, inducing a transient thermal effect in the applied tape by thermally heating the tape using an infrared source; or by cooling with a stream of cooled air.

21. The method of claim 1, wherein said thermographic imaging component comprises UV imaging for crystallinity determination in a thermoplastic component or structure.

22. The method of claim 1, including situating a field imaging camera in a location to image the location where the thermoformable material component is added to build the structure, and imaging with the field imaging camera the real-time locations of at least the thermographic imaging component, the thermoformable material component being applied and the structure to which the thermoformable material component is being applied.

23. The method of claim 22, wherein the structure is constructed using one or more robots, wherein said thermoformable material component is robotically applied by operating said one or more robots to form the structure wherein the thermographic imaging component comprises a thermal (IR) camera, wherein a file containing CAD coordinates of the structure being constructed is provided; and wherein the method includes using dynamic photogrammetry calibrated to track the thermal (IR) camera, and infer the precise location of detected defects in the structure coordinates, such as CAD coordinates, and wherein imaging with the field imaging camera images photogrammetry targets located on at least the thermographic imaging component and at least one of the said one or more robots.

24. The method of claim 1, including implementing one or more processing steps in a construction operation to construct the structure, wherein at least one of the processing steps comprises applying at least one of the thermoformable material to construct the structure wherein the thermoformable material forms a bond, and monitoring the bonding process via monitoring the application of the thermoformable material and its bond to the structure or other component to determine the sufficiency or quality of the bond, and wherein when the monitored sufficiency or quality of the bond does not meet a threshold for sufficiency or quality, then controlling at least one or more other processing steps to cease use of the structure.

25. The method of claim 24, wherein said one or more process steps are automated, wherein applying at least one of the thermoformable material to construct the structure is automated with a robot, and wherein at least one or more other processing steps are automated with a robot that comprises the same or a different robot, and wherein when the monitored sufficiency or quality of the bond does not meet a threshold for sufficiency or quality, instructing the same or the said different robot to cease further processing of the structure.

26. The method of claim 1, wherein said structure is comprised of a plurality of thermoformable composite components that are applied as adjacent layers on top of each other, and wherein said adjacent layers form a bond between each layer, and wherein said capturing with the imaging device is carried out as each component layer of thermoformable material is applied to construct the structure, and wherein step d is carried out d) processing the captured information from step a) in step d is carried out by applying cooling to the component layer when it is applied to the structure, and monitoring the bond quality by determining a differential of heat flux of the applied component heating after the application of cooling to the thermoformable component layer when it is applied to the structure, wherein said application of cooling comprises directing a cool gas at the layer, and wherein imaging of the thermoformable component layer when it is applied to the structure is carried out to capture the cooled layer returning to an elevated temperature.

27. The method of claim 1, wherein the method comprises a continuous operation carried out during the construction of the structure.

* * * * *